US009316913B2

(12) United States Patent
Echigo et al.

(10) Patent No.: US 9,316,913 B2
(45) Date of Patent: Apr. 19, 2016

(54) UNDERLAYER FILM-FORMING MATERIAL FOR LITHOGRAPHY, UNDERLAYER FILM FOR LITHOGRAPHY, AND PATTERN FORMATION METHOD

(75) Inventors: Masatoshi Echigo, Hiratsuka (JP); Go Higashihara, Kurashiki (JP); Naoya Uchiyama, Kurashiki (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 124 days.

(21) Appl. No.: 14/238,442

(22) PCT Filed: Aug. 9, 2012

(86) PCT No.: PCT/JP2012/070305
§ 371 (c)(1),
(2), (4) Date: Apr. 21, 2014

(87) PCT Pub. No.: WO2013/024779
PCT Pub. Date: Feb. 21, 2013

(65) Prior Publication Data
US 2015/0090691 A1  Apr. 2, 2015

(30) Foreign Application Priority Data

Aug. 12, 2011 (JP) ................................ 2011-176923
Sep. 15, 2011 (JP) ................................ 2011-201757
Sep. 30, 2011 (JP) ................................ 2011-218440

(51) Int. Cl.
| | | |
|---|---|---|
| G03F 7/09 | (2006.01) | |
| C07D 311/96 | (2006.01) | |
| C08G 8/04 | (2006.01) | |
| G03F 7/30 | (2006.01) | |
| G03F 7/40 | (2006.01) | |

(52) U.S. Cl.
CPC .............. *G03F 7/091* (2013.01); *C07D 311/96* (2013.01); *C08G 8/04* (2013.01); *G03F 7/094* (2013.01); *G03F 7/30* (2013.01); *G03F 7/40* (2013.01)

(58) Field of Classification Search
None
See application file for complete search history.

(56) References Cited

U.S. PATENT DOCUMENTS

| | | |
|---|---|---|
| 2002/0106909 A1 | 8/2002 | Kato et al. |
| 2003/0092852 A1* | 5/2003 | Ogura et al. ............ 525/403 |
| 2005/0074695 A1 | 4/2005 | Nakamura et al. |
| 2005/0255712 A1 | 11/2005 | Kato et al. |
| 2007/0172759 A1 | 7/2007 | Ogihara et al. |
| 2010/0316950 A1 | 12/2010 | Oguro et al. |
| 2012/0171611 A1 | 7/2012 | Ideno et al. |

FOREIGN PATENT DOCUMENTS

| | | | |
|---|---|---|---|
| EP | 1300403 A1 | | 4/2003 |
| JP | 01283280 A | * | 11/1989 |
| JP | 2002334869 A | | 11/2002 |
| JP | 2002334896 A | | 11/2002 |
| JP | 2004177668 A | | 6/2004 |
| JP | 2004271838 A | | 9/2004 |
| JP | 2005250434 A | | 9/2005 |
| JP | 2006-036648 A | | 2/2006 |
| JP | 2006213634 A | | 8/2006 |
| JP | 2007-199653 A | | 8/2007 |
| JP | 2007226170 A | | 9/2007 |
| JP | 2007226204 A | | 9/2007 |
| JP | 2007326847 A | | 12/2007 |
| JP | 2008239868 A | * | 10/2008 |
| JP | 2009155256 A | | 7/2009 |
| JP | 2010-170013 A | | 8/2010 |
| JP | 2011068624 A | | 4/2011 |
| JP | 2011105887 A | | 6/2011 |
| WO | 2004066377 A1 | | 8/2004 |
| WO | 2007-097457 A1 | | 8/2007 |
| WO | 2009072465 A1 | | 6/2009 |
| WO | 2011034062 A1 | | 3/2011 |

OTHER PUBLICATIONS written translation JP H01-283280. Nov. 14, 1989.*
machine translation JP 2008-129868. Oct. 9, 2008.*
Okan Sirkecioğ; Lu, et al: "A Novel Synthesis of 14-(Hydroxymethylalkyl) Derivatives of Dibenxoanthenes and 3,3-Dimethyl-4-(2-hydroxy-1-naphthyl)benzo[f]chroman", Journal of Heterocyclic Chemistry, vol. 35, No. 2, Mar. 1, 1998, pp. 457-460, XP055169545, ISSN: 0022-152X, DOI: 10.1002/hjet.5570350232.
International Search Report, Sep. 11, 2012.

* cited by examiner

*Primary Examiner* — Cynthia H Kelly
*Assistant Examiner* — Alyssa L Cepluch
(74) *Attorney, Agent, or Firm* — Fitch, Even, Tabin & Flannery LLP

(57) ABSTRACT

Material for forming an underlayer film for lithography, which has a high carbon concentration, a low oxygen concentration, a relatively high heat resistance and also a relatively high solvent solubility, and which can be applied to a wet process is disclosed. Material for forming an underlayer film for lithography contains a compound represented by general formula (1).

9 Claims, No Drawings

UNDERLAYER FILM-FORMING MATERIAL FOR LITHOGRAPHY, UNDERLAYER FILM FOR LITHOGRAPHY, AND PATTERN FORMATION METHOD

CROSS-REFERENCE TO RELATED APPLICATIONS

This Application is a U.S. National Stage Application filed under 35 U.S.C. §371 of International Application PCT/JP2012/070305, filed Aug. 9, 2012, designating the United States, which claims priority from Japanese Patent Application 2011-176923, filed Aug. 12, 2011, Japanese Patent Application 2011-201757, filed Sep. 15, 2011, and Japanese Patent Application 2011-218440, filed Sep. 30, 2011, the complete disclosures of which are hereby incorporated herein by reference in their entirety for all purposes.

TECHNICAL FIELD

The present invention relates to a material for forming an underlayer film for lithography, the material containing a compound or resin of a specified structure, and relates to a forming method of a photoresist pattern using the material for forming an underlayer film for lithography.

BACKGROUND ART

Semiconductor devices are manufactured through microfabrication by lithography using a photoresist material, but are required to be made finer by a pattern rule in accordance with the increase in integration degree and the increase in speed of LSI in recent years. In lithography using exposure to light, which is currently used as a general-purpose technique, the resolution is now approaching the intrinsic limitation associated with the wavelength of the light source.

A light source for lithography, for use in forming a resist pattern, has a shorter wavelength from a KrF excimer laser (248 nm) to an ArF excimer laser (193 nm). However, as the resist pattern is made finer and finer, there arise a problem of resolution and a problem of collapse of the resist pattern after development, and therefore there is demanded for making a resist film thinner. On the other hand, if the resist film is merely made thinner, it is difficult to achieve the resist pattern having a film thickness sufficient for processing a substrate. Accordingly, there is increasingly required a process in which not only the resist pattern but also a resist underlayer film is prepared between a resist and a semiconductor substrate to be processed and the resist underlayer film is allowed to have a function as a mask at the time of processing the substrate.

Currently, as the resist underlayer film for such a process, various ones are known. For example, in order to provide a resist underlayer film for lithography, having a selection ratio of dry etching rate close to the resist, unlike a conventional resist underlayer film having a high etching rate, there has been proposed a material for forming an underlayer film for multilayer resist process, containing a resin component having at least a substituent which releases a terminal group to form a sulfonic acid residue when a predetermined energy is applied, and a solvent (see Patent Literature 1). In addition, in order to provide a resist underlayer film for lithography, having a smaller selection ratio of dry etching rate than the resist, there has been proposed a resist underlayer film material including a polymer having a specified repeating unit (see Patent Literature 2). Furthermore, in order to provide a resist underlayer film for lithography, having a smaller selection ratio of dry etching rate than the semiconductor substrate, there has been proposed a resist underlayer film material including a polymer formed by co-polymerizing a repeating unit of acenaphthylene and a substituted or non-substituted repeating unit having a hydroxy group (see Patent Literature 3).

On the other hand, as a material for allowing such a resist underlayer film to have a high etching resistance, an amorphous carbon underlayer film is well known, which is formed by CVD using methane gas, ethane gas, acetylene gas, or the like as a raw material. However, there is demanded, in terms of process, a resist underlayer film material that can form a resist underlayer film in a wet process such as a spin coating method or screen printing.

In addition, as a material that is excellent in optical characteristics and etching resistance and that is capable of being dissolved in a solvent and being applied to a wet process, the present inventors have proposed a composition for forming an underlayer film for lithography, which contains a naphthalene formaldehyde polymer including a specified constituent unit, and an organic solvent (see Patent Literatures 4 and 5).

Meanwhile, with respect to a forming method of an intermediate layer for use in forming a resist underlayer film in a three-layer process, for example, known are a forming method of a silicon nitride film (see Patent Literature 6), and a CVD forming method of a silicon nitride film (see Patent Literature 7). In addition, as an intermediate layer material for a three-layer process, known is a material containing a silsesquioxane-based silicon compound (see Patent Literatures 8 and 9).

CITATION LIST

Patent Literature

Patent Literature 1: Japanese Patent Laid-Open No. 2004-177668
Patent Literature 2: Japanese Patent Laid-Open No. 2004-271838
Patent Literature 3: Japanese Patent Laid-Open No. 2005-250434
Patent Literature 4: International Publication No. WO 2009/072465
Patent Literature 5: International Publication No. WO 2011/034062
Patent Literature 6: Japanese Patent Laid-Open No. 2002-334869
Patent Literature 7: International Publication No. WO 2004/066377
Patent Literature 8: Japanese Patent Laid-Open No. 2007-226170
Patent Literature 9: Japanese Patent Laid-Open No. 2007-226204

SUMMARY OF INVENTION

Technical Problem

As described above, many materials for forming an underlayer film for lithography have been conventionally proposed, but there are no ones that not only have such a high solvent solubility as to be able to be applied to a wet process such as a spin coating method or screen printing, but also simultaneously satisfy heat resistance and etching resistance at a high level, and thus a new material is required to be developed.

The present invention has been made in view of the above problem, and an object thereof is to provide a material for forming an underlayer film for lithography, which can be applied to a wet process and which is useful for forming a photoresist underlayer film excellent in heat resistance and etching resistance, and a pattern forming method using the material.

Solution to Problem

The present inventors have intensively studied to solve the above problem, and as a result, have found that the above problem can be solved by using a naphthol derivative of a specified structure (compound or resin), thereby leading to the completion of the present invention.

That is, the present invention provides the following <1> to <9>.

<1> A material for forming an underlayer film for lithography, containing a compound represented by the following general formula (1).

[Formula 1]

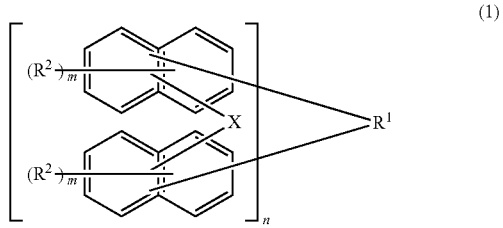

(1)

(in formula (1), each X independently represents an oxygen atom or a sulfur atom, each $R^1$ independently represents a single bond or a 2n-valent hydrocarbon group having 1 to 30 carbon atoms, the hydrocarbon group may have a cyclic hydrocarbon group, a double bond, a hetero atom, or an aromatic group having 6 to 30 carbon atoms, and each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group, each m is independently an integer of 1 to 6, and n is an integer of 1 to 4.)

<2> The material for forming an underlayer film for lithography according to <1>, wherein the compound represented by the general formula (1) is a compound represented by the following general formula (1a).

[Formula 2]

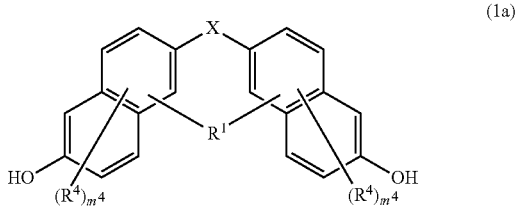

(1a)

(in formula (1a), each X independently represents an oxygen atom or a sulfur atom, each $R^1$ independently represents a single bond or a 2n-valent hydrocarbon group having 1 to 30 carbon atoms, the hydrocarbon group may have a cyclic hydrocarbon group, a double bond, a hetero atom, or an aromatic group having 6 to 30 carbon atoms, each $R^4$ independently represents a linear, branched or cyclic alkyl group having 1 to 10 carbon atoms, an aryl group having 6 to 10 carbon atoms, an alkenyl group having 2 to 10 carbon atoms, or a hydroxyl group, and each $m^4$ is independently an integer of 0 to 5.)

<3> A material for forming an underlayer film for lithography, containing a resin having a structure represented by the following general formula (2).

[Formula 3]

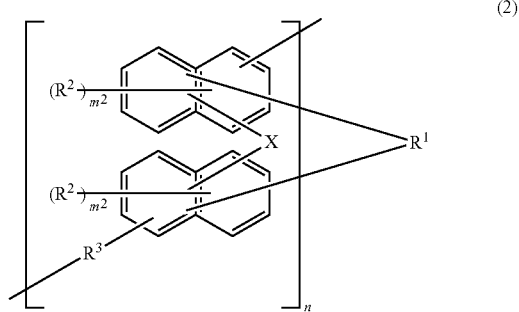

(2)

(in formula (2), each X independently represents an oxygen atom or a sulfur atom, each $R^1$ independently represents a single bond or a 2n-valent hydrocarbon group having 1 to 30 carbon atoms, the hydrocarbon group may have a cyclic hydrocarbon group, a double bond, a hetero atom, or an aromatic group having 6 to 30 carbon atoms, and each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group, each $R^3$ independently represents a single bond, or a linear or branched alkylene group having 1 to 20 carbon atoms, each $m^2$ is independently an integer of 1 to 5, and n is an integer of 1 to 4.)

<4> The material for forming an underlayer film for lithography according to any one of <1> to <3>, further containing an organic solvent.

<5> The material for forming an underlayer film for lithography according to any one of <1> to <4>, further containing an acid generating agent.

<6> The material for forming an underlayer film for lithography according to any one of <1> to <5>, further containing a crosslinking agent.

<7> An underlayer film for lithography, formed from the material for forming an underlayer film for lithography according to any one of <1> to <6>.

<8> A pattern forming method including forming an underlayer film on a substrate by using the material for forming an underlayer film according to any one of <1> to <6>, forming at least one photoresist layer on the underlayer film, then irradiating a required region of the photoresist layer with radiation, followed by developing with an alkali.

<9> A pattern forming method including forming an underlayer film on a substrate by using the material for forming an underlayer film according to any one of <1> to <6>, forming an intermediate layer film on the underlayer film by using a silicon atom-containing resist intermediate layer film material, forming at least one photoresist layer on the intermediate layer film, then irradiating a required region of the photoresist layer with radiation, followed by developing with an alkali to form a resist pattern, and thereafter etching the intermediate layer film while the resist pattern functions as a mask, etching the underlayer film while the obtained intermediate layer film pattern functions as an etching mask and etching the substrate while the obtained underlayer film pattern functions as an etching mask, to form a pattern on the substrate.

Advantageous Effects of Invention

According to the present invention, it is possible to provide a material for forming an underlayer film for lithography, which can be applied to a wet process and which is useful for forming a photoresist underlayer film excellent in heat resistance and etching resistance. Since the material for forming an underlayer film for lithography is formed using a naphthol derivative of a specified structure (compound or resin) which has a high heat resistance, a relatively high carbon concentration, a relatively low oxygen concentration, and also a high solvent solubility, the material can be used to form an underlayer film whose degradation is suppressed at high-temperature baking and which is also excellent in etching resistance to oxygen plasma etching or the like, and further to obtain an excellent resist pattern because the underlayer film is excellent in adhesiveness with a resist layer.

DESCRIPTION OF EMBODIMENTS

Hereinafter, embodiments of the present invention will be described. It is to be noted that the following embodiments are illustrative for describing the present invention, and the present invention is not limited only to the embodiments.
(Material for Forming Underlayer Film for Lithography)

A material for forming an underlayer film for lithography according to the present embodiment contains at least a compound represented by the following general formula (1).

[Formula 4]

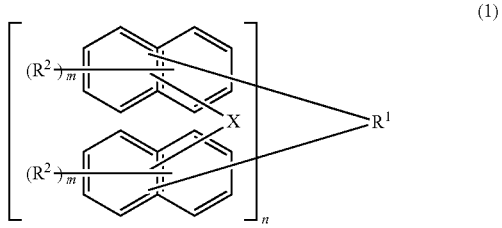

(1)

In the formula (1), each X independently represents an oxygen atom or a sulfur atom, and respective naphthalene rings are bonded with each other via X. Each $R^1$ independently represents a single bond or a 2n-valent hydrocarbon group having 1 to 30 carbon atoms, and respective naphthalene rings are bonded with each other via $R^1$. Herein, the 2n-valent hydrocarbon group may have a cyclic hydrocarbon group, a double bond, a hetero atom, or an aromatic group having 6 to 30 carbon atoms. Each $R^2$ independently represents a monovalent substituent selected from the group consisting of a linear, branched or cyclic alkyl group having 1 to 10 carbon atoms, an aryl group having 6 to 10 carbon atoms, an alkenyl group having 2 to 10 carbon atoms, and a hydroxyl group, and m number of $R^2$(s) is bonded to each naphthalene ring. Herein, at least one $R^2$ represents a hydroxyl group. In addition, each m is independently an integer of 1 to 6, and n is an integer of 1 to 4.

Herein, the 2n-valent hydrocarbon group means an alkylene group having 1 to 30 carbon atoms when n=1, an alkanetetrayl group having 1 to 30 carbon atoms when n=2, an alkanehexayl group having 2 to 30 carbon atoms when n=3, and an alkaneoctayl group having 3 to 30 carbon atoms when n=4. Examples of the 2n-valent hydrocarbon group include those having a linear, branched or cyclic structure.

In addition, the 2n-valent hydrocarbon group may have a cyclic hydrocarbon group, a double bond, a hetero atom, or an aromatic group having 6 to 30 carbon atoms. Herein, the cyclic hydrocarbon group also includes a bridged cyclic hydrocarbon group.

The compound represented by general formula (1) has a high heat resistance due to rigidity of its structure while having a relatively low molecular weight, and therefore it can be used even under a high-temperature baking condition. In addition, the compound has a relatively low molecular weight and a low viscosity, and therefore, even when being applied to a substrate having a step (in particular, fine space, hole pattern and the like), it can be easily filled uniformly in every part of the step. As a result, a material for forming an underlayer film for lithography using such a compound can be improved in terms of embedding properties in a relatively advantageous manner. In addition, the compound has a relatively high carbon concentration to thereby impart also a high etching resistance.

Herein, the compound represented by the general formula (1) is preferably a compound represented by the following formula (1-1).

[Formula 5]

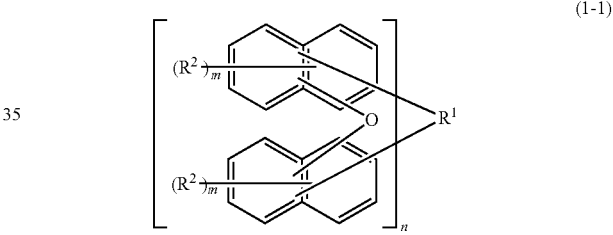

(1-1)

In the formula (1-1), $R^1$, $R^2$, m, and n are the same as defined in the formula (1).

In addition, the compound represented by the general formula (1-1) is more preferably a compound represented by the following formula (1-2).

[Formula 6]

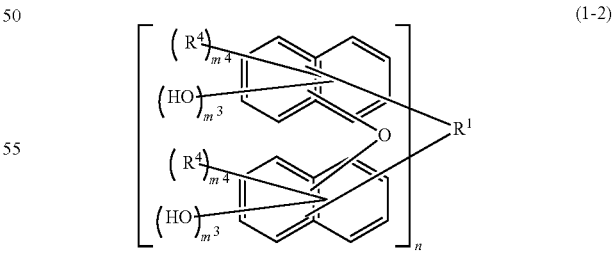

(1-2)

In the formula (1-2), $R^1$ and n are the same as defined in the formula (1-1), $R^4$ is the same as $R^2$ in the formula (1), each $m_3$ is independently an integer of 1 to 6, each $m_4$ is independently an integer of 0 to 5, and $m_3+m_4$ is an integer of 1 to 6.

The compound represented by the general formula (1-2) is further preferably a compound represented by the following formula (1-3).

[Formula 7]

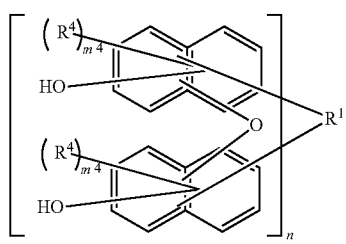
(1-3)

In the formula (1-3), $R^1$, $R^4$, and $m^4$ are the same as defined in the formula (1-2).

In addition, the compound represented by the general formula (1) is preferably a mode where n=1 in the formula (1), namely, a compound represented by the following general formula (1a), in terms of having a low molecular weight.

[Formula 8]

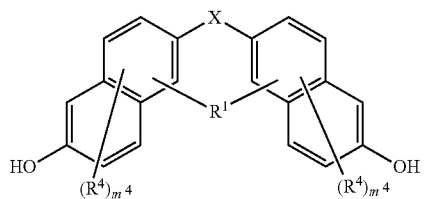
(1a)

In the formula (1a), X, $R^1$, $R^4$, and $m^4$ are the same as defined in the formula (1-2).

Furthermore, the compound represented by the general formula (1a) is particularly preferably a mode where X=O in the formula (1a), namely, a compound represented by the following formula (1-4).

[Formula 9]

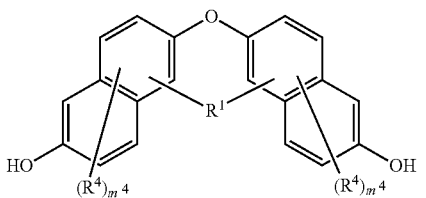
(1-4)

In the formula (1-4), $R^1$, $R^4$, and $m^4$ are the same as defined in the formula (1a).

Specific examples of the compound represented by the general formula (1) include the following, but not limited to those recited herein.

[Formula 10]

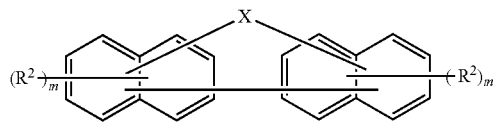

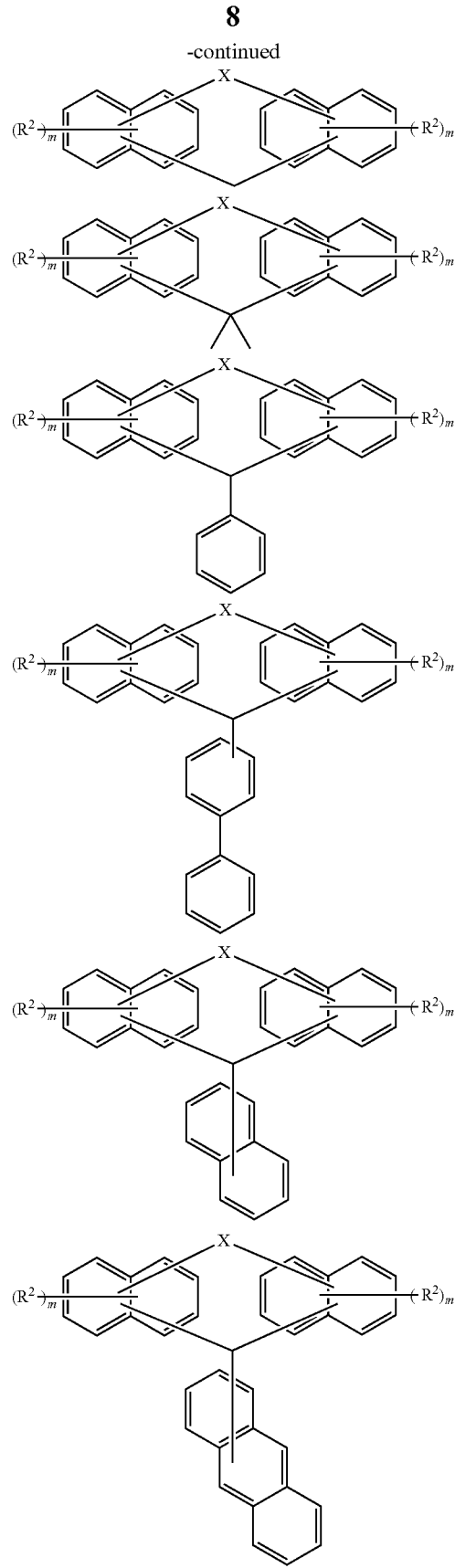

(wherein $R^2$, X, and m are the same as defined in the formula (1).)

[Formula 11]
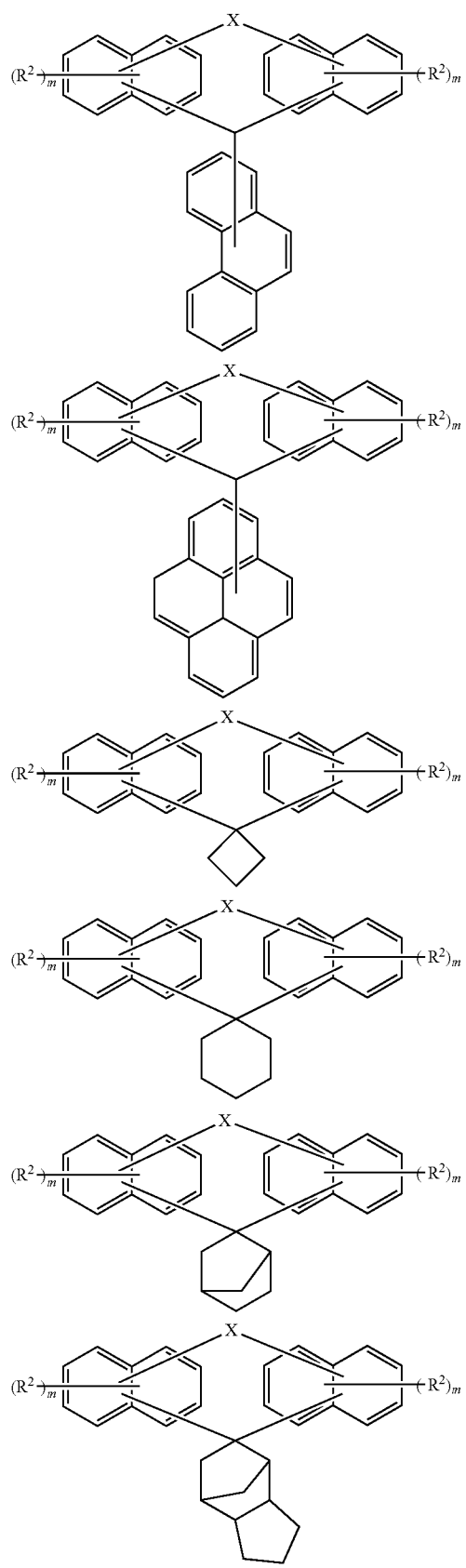
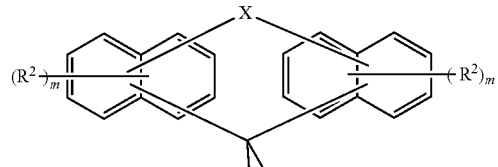
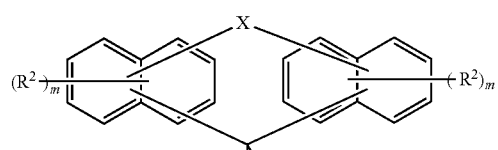
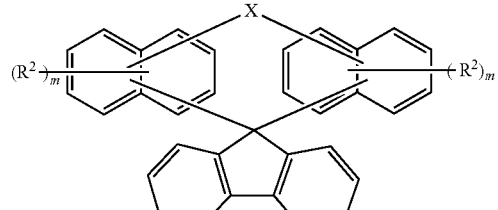
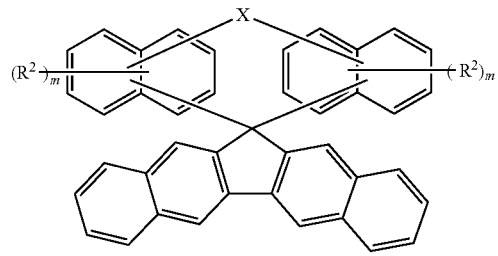
(wherein $R^2$, X, and m are the same as defined in the formula (1).)
[Formula 12]
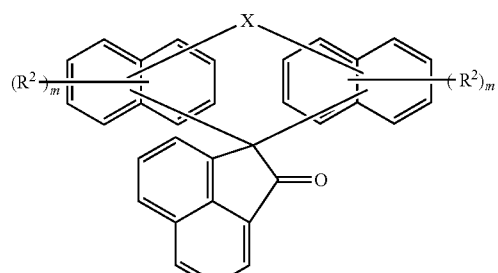
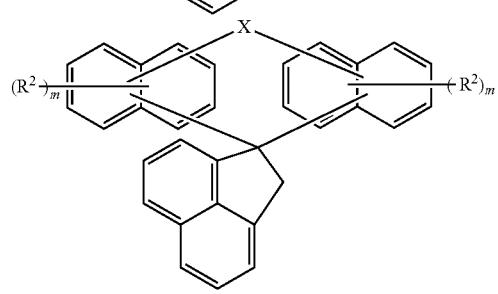

-continued
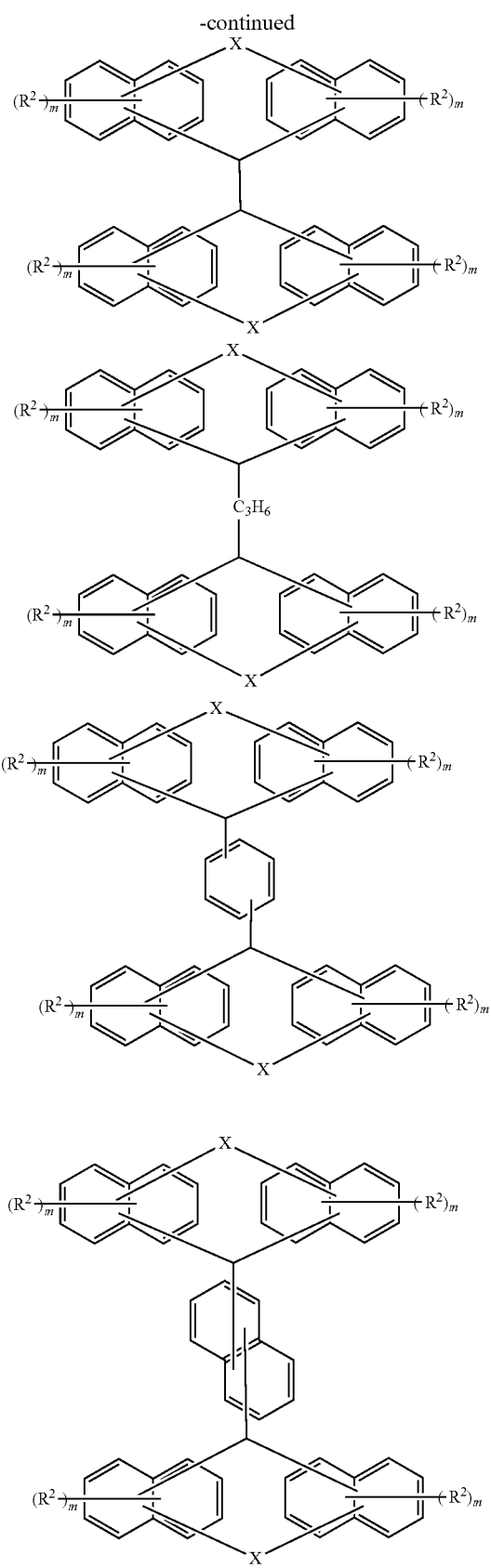
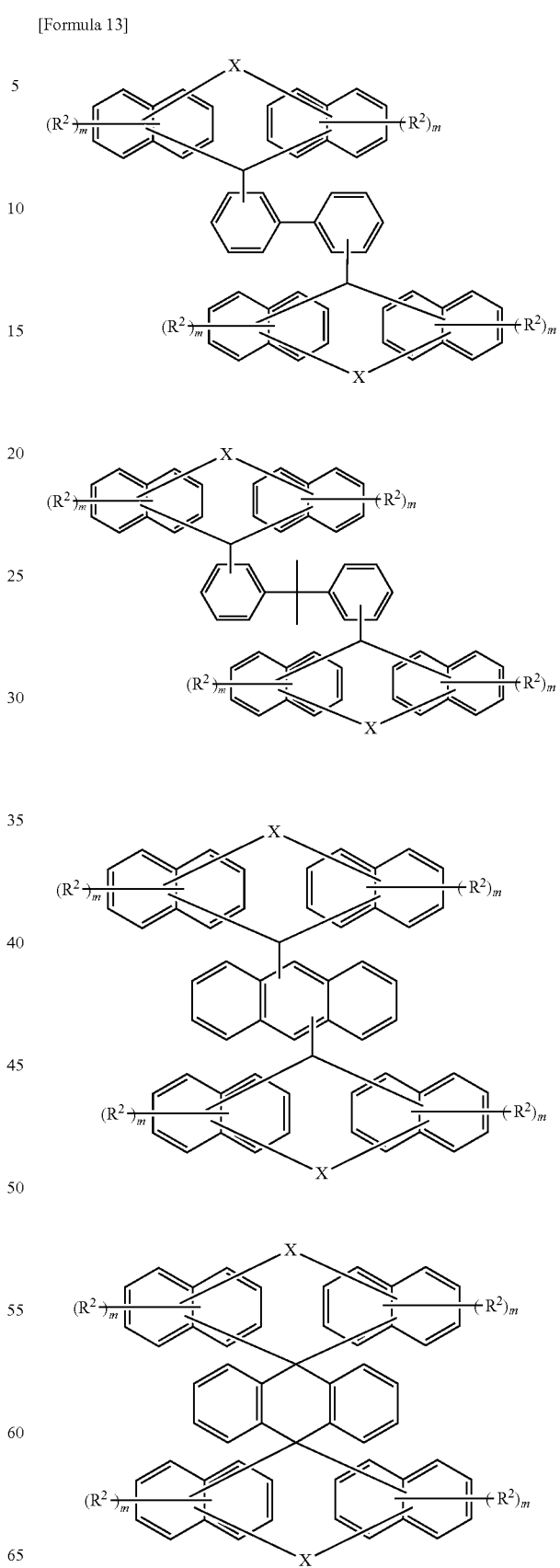
(wherein $R^2$, X, and m are the same as defined in the formula (1).)

-continued
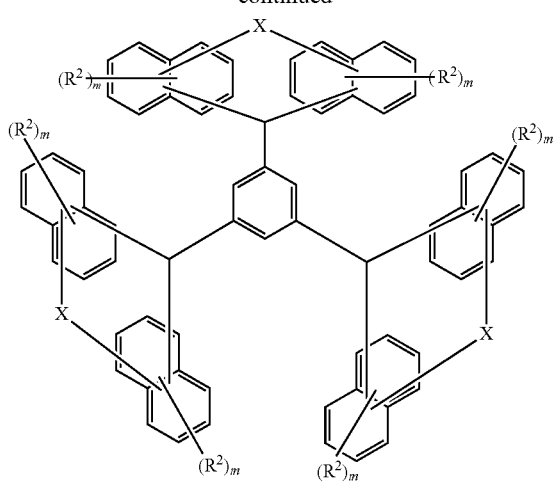
(wherein R², X, and m are the same as defined in the formula (1).)
Specific examples of the compound represented by the general formula (1) further include the following, but not limited to those recited herein.
[Formula 14]
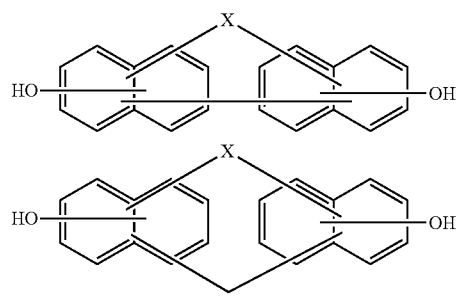
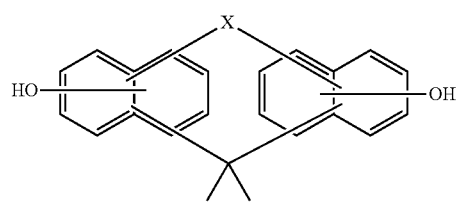
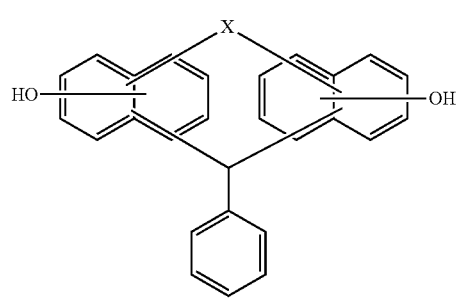
-continued
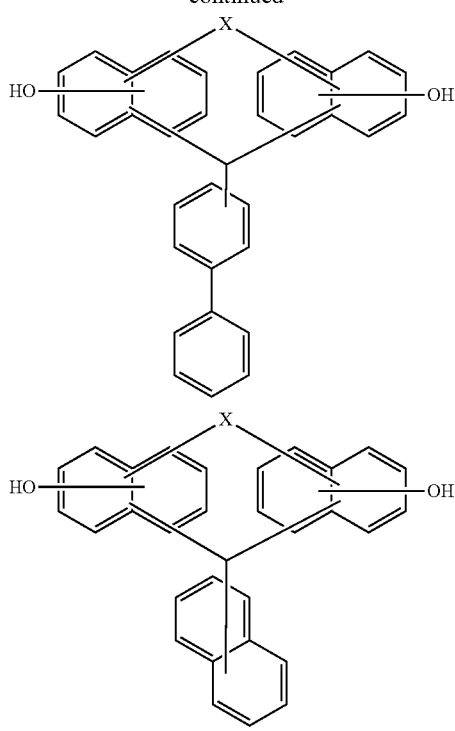
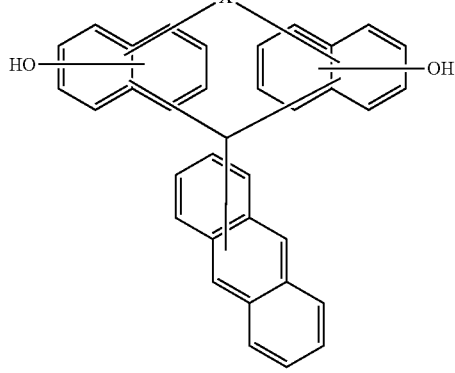
(wherein X is the same as defined in the formula (1).)
[Formula 15]
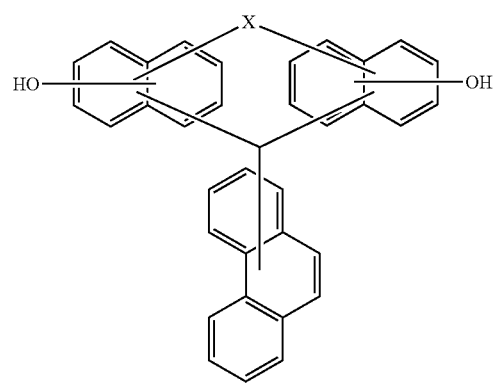

-continued
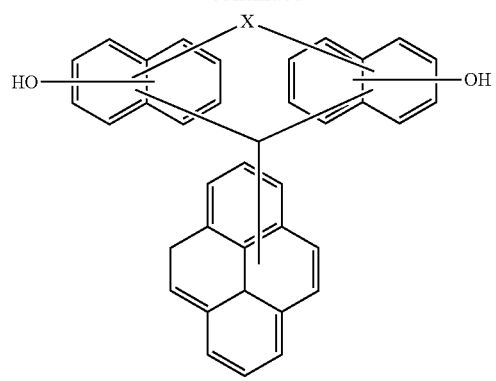
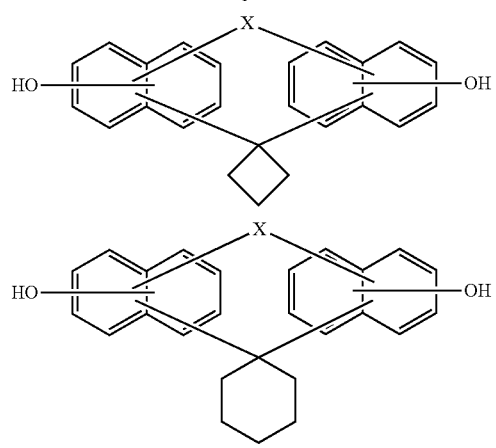
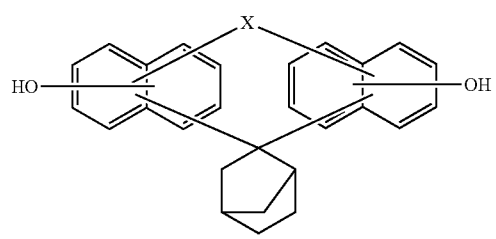
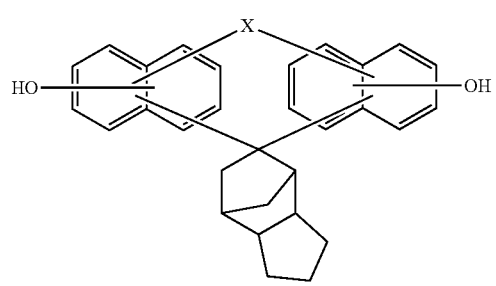
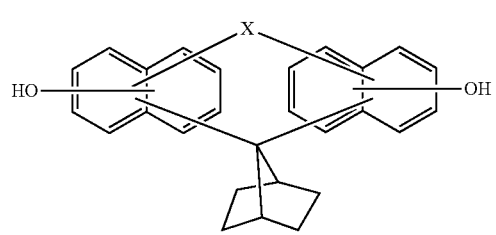
-continued
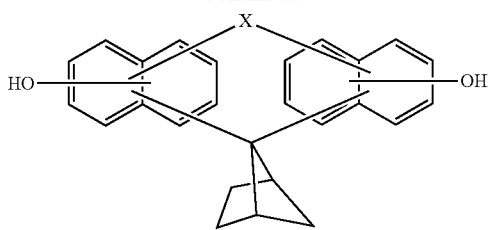
(wherein X is the same as defined in the formula (1).)
[Formula 16]
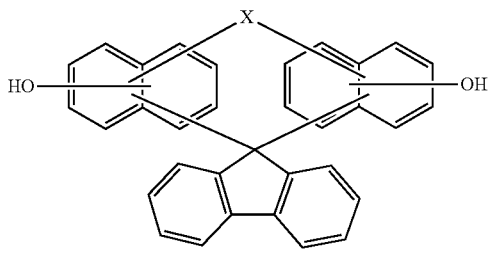
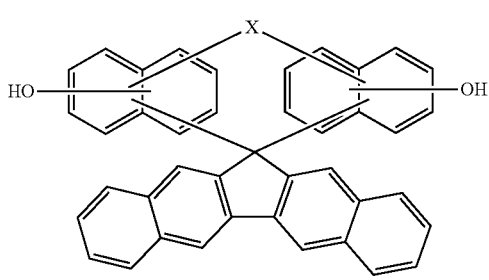
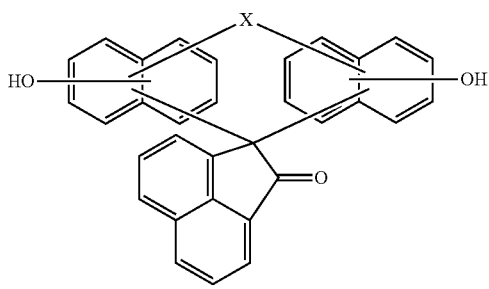
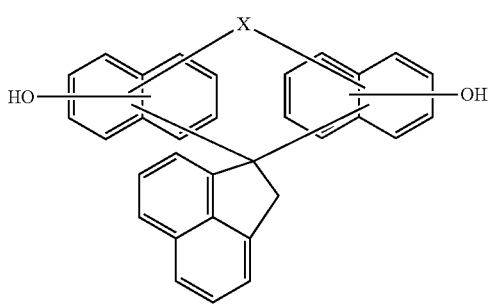

-continued
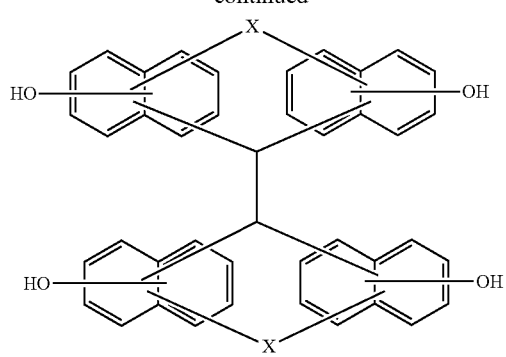
(wherein X is the same as defined in the formula (1).)
[Formula 17]
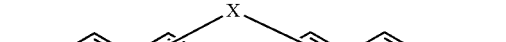
-continued
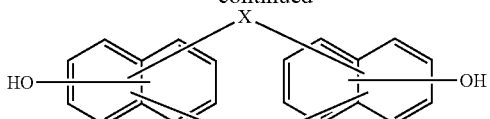
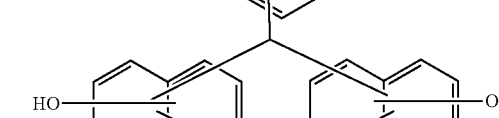
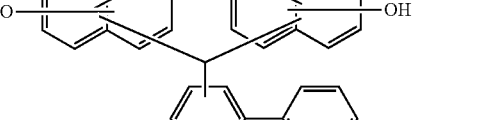
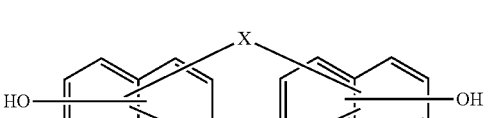
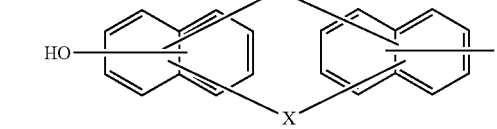

-continued

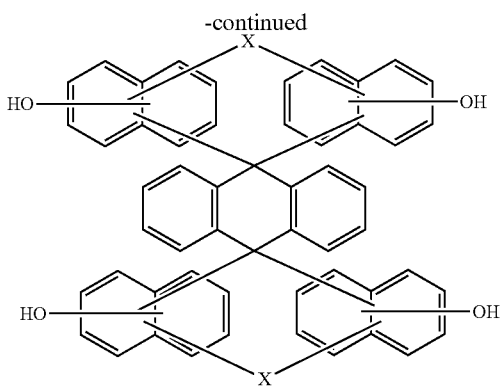

(wherein X is the same as defined in the formula (1).)

[Formula 18]

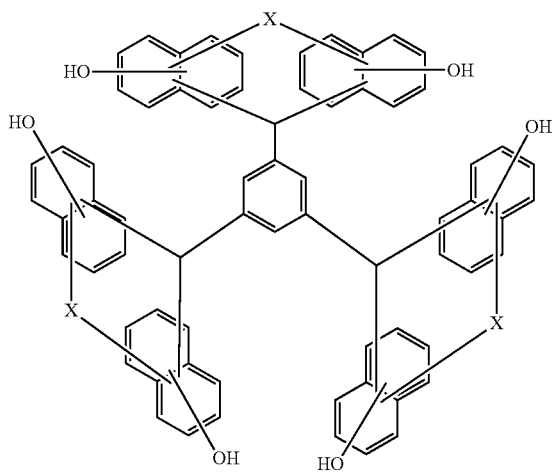

(wherein X is the same as defined in the formula (1).)

The compound represented by the general formula (1) can be appropriately synthesized by applying a known method, and a synthesis method thereof is not particularly limited. For example, naphthols or thionaphthols and the corresponding aldehydes or ketones can be subjected to a polycondensation reaction under ordinary pressure in the presence of an acid catalyst to thereby provide the compound represented by the general formula (1). The reaction can also be performed under pressure, if necessary.

Examples of the naphthols include naphthol, methylnaphthol, methoxynaphthol, and naphthalenediol, but are not particularly limited thereto. These can be used alone, or two or more thereof can be used in combination. Among them, naphthalenediol is more preferably used from the viewpoint of being capable of easily making a xanthene structure.

Examples of the thionaphthols include naphthalenethiol, methyl naphthalenethiol, methoxy naphthalenethiol, and naphthalenedithiol, but are not particularly limited thereto. These can be used alone, or two or more thereof can be used in combination. Among them, naphthalenedithiol is more suitably used from the viewpoint of being capable of easily making a thioxanthene structure.

Examples of the aldehydes include formaldehyde, trioxane, paraformaldehyde, acetaldehyde, propylaldehyde, butylaldehyde, hexylaldehyde, decylaldehyde, undecylaldehyde, phenylacetaldehyde, phenylpropylaldehyde, furfural, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, bis(diformylphenyl)methane, bis(diformylphenyl)propane, and benzenetricarboxaldehyde, but are not particularly limited thereto. These can be used alone, or two or more thereof can be used in combination. Among them, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, anthracenedicarboxaldehyde, bis(diformylphenyl)methane, bis(diformylphenyl)propane, or benzenetricarboxaldehyde is preferably used from the viewpoint of imparting a high heat resistance.

Examples of the ketones include acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, and anthraquinone, but are not particularly limited thereto. These can be used alone, or two or more thereof can be used in combination. Among them, cyclopentanone, cyclohexanone, norbornanone, tricyclohexanone, tricyclodecanone, adamantanone, fluorenone, benzofluorenone, acenaphthenequinone, acenaphthenone, or anthraquinone is preferably used from the viewpoint of imparting a high heat resistance.

The acid catalyst for use in the above reaction can be appropriately selected from known ones and used, and is not particularly limited. Such an acid catalyst is an inorganic acid or an organic acid, as widely known, and examples thereof include inorganic acids such as hydrochloric acid, sulfuric acid, phosphoric acid, hydrobromic acid, or hydrofluoric acid, organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, or naphthalenedisulfonic acid, Lewis acids such as zinc chloride, aluminum chloride, iron chloride, or boron trifluoride, or solid acids such as tungstosilicic acid, tungstophosphoric acid, silicomolybdic acid, or phosphomolybdic acid, but are not particularly limited thereto. Among them, organic acids and solid acids are preferable in terms of production, and hydrochloric acid or sulfuric acid is preferably used in terms of production such as availability or handleability. Herein, these acid catalysts can be used alone, or two or more thereof can be used in combination. In addition, the amount of the acid catalyst to be used can be appropriately set depending on the types of raw materials to be used and the catalyst to be used, reaction conditions, and the like, and is not particularly limited, but the amount is preferably 0.01 to 100 parts by mass based on 100 parts by mass of reaction raw materials.

A reaction solvent may also be used during the above reaction. The reaction solvent that can be used is not particularly limited and is appropriately selected from known ones as long as the reaction of the aldehydes or ketones to be used and the naphthols or thionaphthols to be used progresses.

Examples thereof include water, methanol, ethanol, propanol, butanol, tetrahydrofuran, dioxane, ethylene glycol dimethyl ether, ethylene glycol diethyl ether, or a mixed solvent thereof. Herein, these solvents can be used alone, or two or more thereof can be used in combination. In addition, the amount of the solvent to be used can be appropriately set depending on the types of raw materials to be used and the catalyst to be used, reaction conditions, and the like, and is not particularly limited, but the amount is preferably 0 to 2000 parts by mass based on 100 parts by mass of reaction raw materials. Furthermore, the reaction temperature in the above reaction can be appropriately selected depending on the reactivity of reaction raw materials, and is not particularly limited, but the reaction temperature usually ranges from 10 to 200° C. In order to form a xanthene structure or a thioxanthene structure as the compound represented by general formula (1) of the present embodiment, the reaction temperature is preferably high and, specifically, preferably ranges from 60 to 200° C. Herein, the reaction method that can be used is appropriately selected from known methods, and is not particularly limited, but includes a method in which the naphthols or thionaphthols, the aldehydes or ketones, and the catalyst are charged at once, and a method in which the naphthols or thionaphthols and the aldehydes or ketones are dropped in the presence of the catalyst. After completion of the polycondensation reaction, the resulting compound can be isolated according to an ordinary method, and the isolation method is not particularly limited. For example, in order to remove the unreacted raw materials and the catalyst present in the system, a common method in which the temperature in a reaction tank is raised to 130 to 230° C. to remove a volatile content at about 1 to 50 mmHg can be adopted to thereby provide an objective compound.

The reaction progresses under such a preferable reaction condition that 1 mol to an excess amount of the naphthols or thionaphthols and 0.001 to 1 mol of the acid catalyst are used, based on 1 mol of the aldehydes or ketones, and are reacted at ordinary pressure and at 50 to 150° C. for about 20 minutes to 100 hours.

After completion of the reaction, the objective compound can be isolated by a known method. For example, the objective compound, the compound represented by the general formula (1), can be obtained by concentrating a reaction liquid, adding pure water thereto to precipitate a reaction product, cooling the resultant to room temperature followed by filtration for separation, drying a solid obtained by filtration, then separating the solid into the reaction product and a by-product for purification by column chromatography, and performing distilling off of the solvent, filtration and drying.

The molecular weight of the compound represented by the general formula (1) is not particularly limited, but the weight average molecular weight Mw thereof is preferably 350 to 5,000, and more preferably 400 to 3,000.

The compound represented by the general formula (1) can be used as a material for forming an underlayer film for lithography, as it is. In addition, the compound can also be used as an oligomeric resin obtained by reacting the compound with a monomer having crosslinking reactivity. Examples of the oligomeric resin obtained from the compound represented by the general formula (1) include those having a structure represented by the following general formula (2). That is, the material for forming an underlayer film for lithography according to the present embodiment may be one at least containing a resin having a structure represented by the following general formula (2).

[Formula 19]

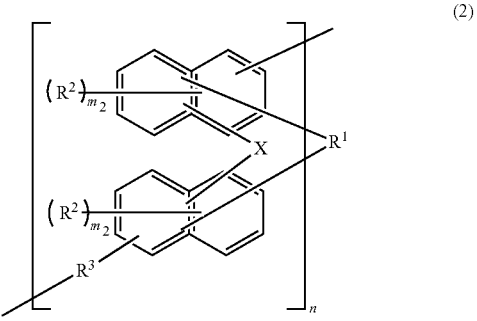

In the formula (2), each X independently represents an oxygen atom or a sulfur atom. Each $R^1$ independently represents a single bond or a 2n-valent hydrocarbon group having 1 to 30 carbon atoms, and the hydrocarbon group may have a cyclic hydrocarbon group, a double bond, a hetero atom, or an aromatic group having 6 to 30 carbon atoms. Each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group. Each $R^3$ independently represents a single bond, or a linear or branched alkylene group having 1 to 20 carbon atoms. Each $m^2$ is independently an integer of 1 to 5, and n is an integer of 1 to 4. Herein, the 2n-valent hydrocarbon group is the same as defined in the formula (1).

The monomer having crosslinking reactivity that can be used is known one without particular limitation as long as the one enables to form an oligomer of the compound represented by the general formula (1). Specific examples thereof include aldehyde, ketone, carboxylic acid, carboxylic halide, a halogen-containing compound, an amino compound, an imino compound, isocyanate, and an unsaturated hydrocarbon group-containing compound, but are not particularly limited thereto.

Specific examples of the resin having a structure represented by general formula (2) include a novolac resin obtained by a condensation reaction of the compound represented by the general formula (1) with an aldehyde as the monomer having crosslinking reactivity, or the like.

Herein, examples of the aldehyde for use in forming the novolac resin of the compound represented by the general formula (1) include formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarbaldehyde, phenanthrenecarbaldehyde, pyrenecarbaldehyde, and furfural, but are not particularly limited thereto. Among them, formaldehyde is more preferable. Herein, these aldehydes can be used alone, or two or more thereof can be used in combination. In addition, the amount of the aldehydes to be used is not particularly limited, but the amount is preferably 0.2 to 5 mol and more preferably 0.5 to 2 mol based on 1 mol of the compound represented by the general formula (1).

A catalyst can also be used in the condensation reaction of the compound represented by the general formula (1) with an aldehyde. The acid catalyst that can be here used is appropriately selected from known ones, and is not particularly limited. Such an acid catalyst is an inorganic acid or an organic acid, as widely known, and examples thereof include inorganic acids such as hydrochloric acid, sulfuric acid, phosphoric acid, hydrobromic acid, or hydrofluoric acid, organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, or naphthalenedisulfonic acid, Lewis acids such as zinc chloride, aluminum chloride, iron chloride, or boron trifluoride, or solid acids such as tungstosilicic acid, tungstophosphoric acid, silicomolybdic acid, or phosphomolybdic acid, but are not particularly limited thereto. Among them, organic acids and solid acids are preferable in terms of production, and hydrochloric acid or sulfuric acid is preferably used in terms of production such as availability or handleability. Herein, these acid catalysts can be used alone, or two or more thereof can be used in combination. In addition, the amount of the acid catalyst to be used can be appropriately set depending on the types of raw materials to be used and the catalyst to be used, reaction conditions, and the like, and is not particularly limited, but the amount is preferably 0.01 to 100 parts by mass based on 100 parts by mass of reaction raw materials. However, in the case of copolymerization with a compound having a non-conjugated double bond, such as indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborna-2-ene, α-pinene, β-pinene, and limonene, the aldehydes are not necessarily required.

A reaction solvent can also be used in the condensation reaction of the compound represented by the general formula (1) with an aldehyde. The reaction solvent in the polycondensation, which can be used, is appropriately selected from known ones, and is not particularly limited, but examples thereof include water, methanol, ethanol, propanol, butanol, tetrahydrofuran, dioxane, or a mixed solvent thereof. Herein, these solvents can be used alone, or two or more thereof can be used in combination. In addition, the amount of the solvent to be used can be appropriately set depending on the types of raw materials to be used and the catalyst to be used, reaction conditions, and the like, and is not particularly limited, but the amount preferably ranges from 0 to 2000 parts by mass based on 100 parts by mass of reaction raw materials. Furthermore, the reaction temperature can be appropriately selected depending on the reactivity of reaction raw materials, and is not particularly limited, but the reaction temperature usually ranges from 10 to 200° C. Herein, the reaction method that can be used is appropriately selected from known methods, and is not particularly limited, but includes a method in which the compound represented by the general formula (1), the aldehydes, and the catalyst are charged at once, and a method in which the compound represented by the general formula (1) and the aldehydes are dropped in the presence of the catalyst. After completion of the polycondensation reaction, the resulting compound can be isolated according to an ordinary method, and the isolation method is not particularly limited. For example, in order to remove the unreacted raw materials and the catalyst present in the system, a common method in which the temperature in a reaction tank is raised to 130 to 230° C. to remove a volatile content at about 1 to 50 mmHg can be adopted to thereby provide an objective novolac resin.

Herein, the resin having a structure represented by the general formula (2) may be a homopolymer of the compound represented by the general formula (1), or may be a copolymer thereof with other phenols. Examples of the copolymerizable phenols include phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol, but are not particularly limited thereto.

In addition, the resin having a structure represented by the general formula (2) may be one obtained by copolymerization with a polymerizable monomer other than the above-described other phenols. Examples of such a copolymerizable monomer include naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornaene, pinene, and limonene, but are not particularly limited thereto. Herein, the resin having a structure represented by the general formula (2) may be a bi or higher functional (for example, bi to tetra) copolymer of the compound represented by the general formula (1) with phenols, a bi or higher functional (for example, bi to tetra) copolymer of the compound represented by the general formula (1) with the above-described copolymerizable monomer, or a ter or higher (for example, ter to tetra) copolymer of the compound represented by the general formula (1), the above-described phenols, and the above-described copolymerizable monomer.

Herein, the molecular weight of the resin having a structure represented by the general formula (2) is not particularly limited, and the weight average molecular weight (Mw) in terms of polystyrene is preferably 500 to 30,000, and more preferably 750 to 20,000. In addition, the resin having a structure represented by the general formula (2) preferably has a dispersity (weight average molecular weight Mw/number average molecular weight Mn) in a range from 1.2 to 7 from the viewpoints of improving a crosslinking efficiency and suppressing a volatile component during baking.

The compound represented by general formula (1) and/or the resin having a structure represented by the general formula (2) preferably have/has a high solubility in the solvent from the viewpoint of making the application of a wet process easier. More specifically, such a compound and/or resin preferably have/has a solubility of 10% by mass or more in 1-methoxy-2-propanol (PGME) or propylene glycol monomethyl ether acetate (PGMEA). Herein, the solubility in PGME or PGMEA is defined as "Mass of resin/(Mass of resin+Mass of solvent)×100 (% by mass)". For example, in the case where 10 g of the phenolic resin is dissolved in 90 g of PGMEA, the solubility of the phenolic resin in PGMEA is "10% by mass or more", and in the case where the phenolic resin is not dissolved, the solubility is "less than 10% by mass".

In the case where the material for forming an underlayer film for lithography according to the present embodiment contains an organic solvent that is an optional component described later, the contents of the compound represented by general formula (1) and the resin having a structure represented by the general formula (2) are not particularly limited, but the contents are preferably 1 to 33 parts by mass, more preferably 2 to 25 parts by mass, and further preferably 3 to 20 parts by mass, based on 100 parts by mass of the total amount of the components including the organic solvent.

(Other Component)

The material for forming an underlayer film for lithography according to the present embodiment may contain, if necessary, other component such as a crosslinking agent, an acid generating agent, and an organic solvent, other than the compound represented by general formula (1) and/or the resin having a structure represented by the general formula (2). Hereinafter, these optional components will be described.

The material for forming an underlayer film for lithography according to the present embodiment may contain, if necessary, a crosslinking agent from the viewpoint of suppressing intermixing and the like.

Specific examples of the crosslinking agent usable in the present embodiment include a melamine compound, a guanamine compound, a glycoluril compound or urea compound, an epoxy compound, a thioepoxy compound, an isocyanate compound, an azide compound, and a compound including a double bond such as an alkenyl ether group, these compounds being substituted with at least one selected from a methylol group, an alkoxymethyl group, and an acyloxymethyl group, but are not particularly limited thereto. Herein, these crosslinking agents can be used alone, or two or more thereof can be used in combination. While such a crosslinking agent may also be used as an additive, such a crosslinkable group may also be introduced into a polymer side chain as a pendant group. A compound including a hydroxy group can also be used as the crosslinking agent.

Specific examples of the melamine compound include, for example, hexamethylolmelamine, hexamethoxymethylmelamine, a compound in which 1 to 6 methylol groups in hexamethylolmelamine are methoxymethylated or mixtures thereof, and hexamethoxyethylmelamine, hexaacyloxymethylmelamine, a compound in which 1 to 6 methylol groups in hexamethylolmelamine are acyloxymethylated or mixtures thereof. Specific examples of the epoxy compound include, for example, tris(2,3-epoxypropyl)isocyanurate, trimethylolmethane triglycidyl ether, trimethylolpropane triglycidyl ether, and triethylolethane triglycidyl ether.

Specific examples of the guanamine compound include, for example, tetramethylolguanamine, tetramethoxymethylguanamine, a compound in which 1 to 4 methylol groups in tetramethylolguanamine are methoxymethylated or mixtures thereof, and tetramethoxyethylguanamine, tetraacyloxyguanamine, a compound in which 1 to 4 methylol groups in tetramethylolguanamine are acyloxymethylated or mixtures thereof. Specific examples of the glycoluril compound include, for example, tetramethylolglycoluril, tetramethoxyglycoluril, tetramethoxymethylglycoluril, a compound in which 1 to 4 methylol groups in tetramethylolglycoluril are methoxymethylated or mixtures thereof, and a compound in which 1 to 4 methylol groups in tetramethylolglycoluril are acyloxymethylated or mixtures thereof. Specific examples of the urea compound include, for example, tetramethylolurea, tetramethoxymethylurea, a compound in which 1 to 4 methylol groups in tetramethylolurea are methoxymethylated or mixtures thereof, and tetramethoxyethylurea.

Specific examples of the compound including an alkenyl ether group include, for example, ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

In the material for forming an underlayer film for lithography according to the present embodiment, the content of the crosslinking agent is not particularly limited, but the content is preferably 5 to 50 parts by mass and more preferably 10 to 40 parts by mass based on 100 parts by mass of the compound represented by the general formula (1) and the resin having a structure represented by the general formula (2). The content is set within the above preferable range to result in tendencies to suppress the occurrence of the mixing phenomenon with the resist layer, and to result in tendencies to enhance an antireflective effect and improve film formability after crosslinking.

The material for forming an underlayer film for lithography of the present embodiment may also contain, if necessary, an acid generating agent from the viewpoint of further promoting a crosslinking reaction by heat. As the acid generating agent, one for generating an acid by pyrolysis and one for generating an acid by light irradiation are known in the art, and any of them can be used.

The acid generating agent includes:
1) an onium salt of the following general formula (P1a-1), (P1a-2), (P1a-3) or (P1b),
2) a diazomethane derivative of the following general formula (P2),
3) a glyoxime derivative of the following general formula (P3),
4) a bissulfone derivative of the following general formula (P4),
5) a sulfonic acid ester of an N-hydroxyimide compound of the following general formula (P5),
6) a β-ketosulfonic acid derivative,
7) a disulfone derivative,
8) a nitrobenzylsulfonate derivative, and
9) a sulfonic acid ester derivative, but is not particularly limited thereto. Herein, these acid generating agents can be used alone, or two or more thereof can be used in combination.

[Formula 20]

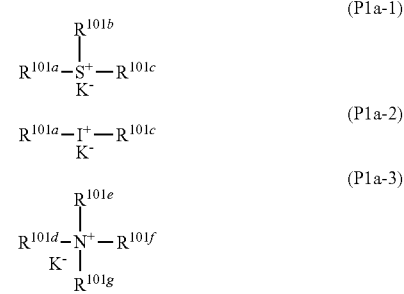

In the above formulae, each of $R^{101a}$, $R^{101b}$ and $R^{101c}$ independently represents a linear, branched or cyclic alkyl group having 1 to 12 carbon atoms, alkenyl group, oxoalkyl group or oxoalkenyl group, an aryl group having 6 to 20 carbon atoms, or an aralkyl group or aryloxoalkyl group having 7 to 12 carbon atoms, and a part or all of hydrogen atoms of these groups may be substituted with an alkoxy group or the like. In addition, $R^{101b}$ and $R^{101c}$ may form a ring, and if forming the ring, each of $R^{101b}$ and $R^{101c}$ independently represents an alkylene group having 1 to 6 carbon atoms. $K^-$ represents a non-nucleophilic counter ion. $R^{101d}$, $R^{101e}$, $R^{101f}$ and $R^{101g}$ are represented by each independently adding a hydrogen atom to $R^{101a}$, $R^{101b}$ and $R^{101c}$, $R^{101d}$ and $R^{101e}$, and $R^{101d}$, $R^{101e}$ and $R^{101f}$ may form a ring, and if forming the ring, $R^{101d}$ and $R^{101e}$, and $R^{101d}$, $R^{101e}$ and $R^{101f}$ represent an alkylene group having 3 to 10 carbon atoms, or a heteroaromatic ring having therein the nitrogen atom(s) in the formula.

$R^{101a}$, $R^{101b}$, $R^{101c}$, $R^{101d}$, $R^{101e}$, $R^{101f}$ and $R^{101g}$ described above may be the same or different from one another. Specifically, the alkyl group includes a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methyl cyclohexyl group, a cyclohexylmethyl group, a norbornyl group, and an adamantyl group. The alkenyl group includes a vinyl group, an allyl group, a propenyl group, a butenyl group, a hexenyl group, and a cyclohexenyl group. The oxoalkyl group includes a 2-oxocyclopentyl group and a 2-oxocyclohexyl group, and can include a 2-oxopropyl group, a 2-cyclopentyl-2-oxoethyl group, a 2-cyclohexyl-2-oxoethyl group, and a 2-(4-methylcyclohexyl)-2-oxoethyl group. The oxoalkenyl group includes a 2-oxo-4-cyclohexenyl group and a 2-oxo-4-propenyl group. The aryl group includes a phenyl group, a naphthyl group, alkoxyphenyl groups such as a p-methoxyphenyl group, a m-methoxyphenyl group, an o-methoxyphenyl group, an ethoxyphenyl group, a p-tert-butoxyphenyl group, and a m-tert-butoxyphenyl group, alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group, alkylnaphthyl groups such as a methylnaphthyl group and an ethylnaphthyl group, alkoxynaphthyl groups such as a methoxynaphthyl group and an ethoxynaphthyl group, dialkylnaphthyl groups such as a dimethylnaphthyl group and a diethylnaphthyl group, and dialkoxynaphthyl groups such as a dimethoxynaphthyl group and a diethoxynaphthyl group. The aralkyl group includes a benzyl group, a phenylethyl group, and a phenethyl group. The aryloxoalkyl group includes 2-aryl-2-oxoethyl groups such as a 2-phenyl-2-oxoethyl group, a 2-(1-naphthyl)-2-oxoethyl group, and a 2-(2-naphthyl)-2-oxoethyl group. The non-nucleophilic counter ion, $K^-$, includes halide ions such as a chloride ion and a bromide ion, fluoroalkyl sulfonates such as triflate, 1,1,1-trifluoroethane sulfonate, and nonafluorobutane sulfonate, aryl sulfonates such as tosylate, benzene sulfonate, 4-fluorobenzene sulfonate, and 1,2,3,4,5-pentafluorobenzene sulfonate, and alkyl sulfonates such as mesylate and butane sulfonate.

In the case where $R^{101d}$, $R^{101e}$, $R^{101f}$ and $R^{101g}$ are each a heteroaromatic ring having the nitrogen atom(s) in the formula, examples of the heteroaromatic ring include imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline and 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivative, and uridine derivatives.

While the general formula (P1a-1) and the general formula (P1a-2) have both effects of a photo acid generating agent and a thermal acid generating agent, the general formula (P1a-3) acts as a thermal acid generating agent.

[Formula 21]

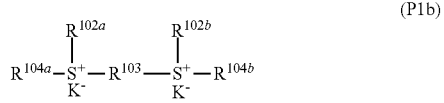

(P1b)

In the formula (P1b), each of $R^{102a}$ and $R^{102b}$ independently represents a linear, branched or cyclic alkyl group having 1 to 8 carbon atoms. $R^{103}$ represents a linear, branched or cyclic alkylene group having 1 to 10 carbon atoms. Each of $R^{104a}$ and $R^{104b}$ independently represents a 2-oxoalkyl group having 3 to 7 carbon atoms. $K^-$ represents a non-nucleophilic counter ion.

Specific examples of $R^{102a}$ and $R^{102b}$ include a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cyclopropylmethyl group, a 4-methyl cyclohexyl group, and a cyclohexylmethyl group. $R^{103}$ includes a methylene group, an ethylene group, a propylene group, a butylene group, a pentylene group, a hexylene group, a heptylene group, an octylene group, a nonylene group, a 1,4-cyclohexylene group, a 1,2-cyclohexylene group, a 1,3-cyclopentylene group, a 1,4-cyclooctylene group, and a 1,4-cyclohexanedimethylene group. $R^{104a}$ and $R^{104b}$ include a 2-oxopropyl group, a 2-oxocyclopentyl group, a 2-oxocyclohexyl group, and a 2-oxocycloheptyl group. $K^-$ includes the same as those described in the formula (P1a-1), (P1a-2) and (P1a-3).

[Formula 22]

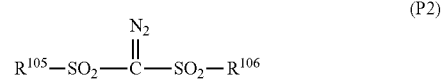

(P2)

In the formula (P2), each of $R^{105}$ and $R^{106}$ independently represents a linear, branched or cyclic alkyl group or halogenated alkyl group having 1 to 12 carbon atoms, an aryl group or halogenated aryl group having 6 to 20 carbon atoms, or an aralkyl group having 7 to 12 carbon atoms.

The alkyl group in each of $R^{105}$ and $R^{106}$ includes a methyl group, an ethyl group, a propyl group, an isopropyl group, a n-butyl group, a sec-butyl group, a tert-butyl group, a pentyl group, a hexyl group, a heptyl group, an octyl group, an amyl group, a cyclopentyl group, a cyclohexyl group, a cycloheptyl group, a norbornyl group, and an adamantyl group. The halogenated alkyl group includes a trifluoromethyl group, a 1,1,1-trifluoroethyl group, a 1,1,1-trichloroethyl group, and a nonafluorobutyl group. The aryl group includes alkoxyphenyl groups such as a phenyl group, a p-methoxyphenyl group, a m-methoxyphenyl group, an o-methoxyphenyl group, an ethoxyphenyl group, a p-tert-butoxyphenyl group, and a m-tert-butoxyphenyl group, and alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group. The halogenated aryl group includes a fluorophenyl group, a chlorophenyl group, and a 1,2,3,4,5-pentafluorophenyl group. The aralkyl group includes a benzyl group and a phenethyl group.

[Formula 23]

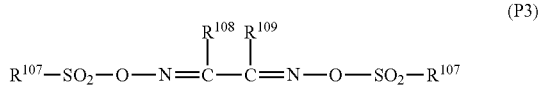
(P3)

In the formula (P3), each of $R^{107}$, $R^{108}$ and $R^{109}$ independently represents a linear, branched or cyclic alkyl group or halogenated alkyl group having 1 to 12 carbon atoms, an aryl group or halogenated aryl group having 6 to 20 carbon atoms, or an aralkyl group having 7 to 12 carbon atoms. $R^{108}$ and $R^{109}$ may be bonded with each other to form a cyclic structure, and if forming the cyclic structure, each of $R^{108}$ and $R^{109}$ represents a linear or branched alkylene group having 1 to 6 carbon atoms.

The alkyl group, halogenated alkyl group, aryl group, halogenated aryl group, and aralkyl group in each of $R^{107}$, $R^{108}$ and $R^{109}$ include the same as those described in $R^{105}$ and $R^{106}$. Herein, the alkylene group in each of $R^{108}$ and $R^{109}$ include a methylene group, an ethylene group, a propylene group, a butylene group, and a hexylene group.

[Formula 24]

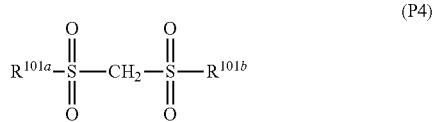
(P4)

In the formula (P4), $R^{101a}$ and $R^{101b}$ are the same as those described above.

[Formula 25]

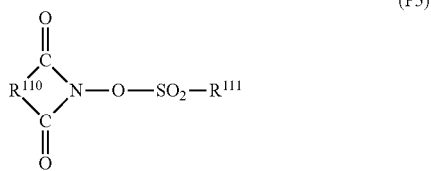
(P5)

In the formula (P5), $R^{110}$ represents an arylene group having 6 to 10 carbon atoms, an alkylene group having 1 to 6 carbon atoms, or an alkenylene group having 2 to 6 carbon atoms, and a part or all of hydrogen atoms of these groups may be further substituted with a linear or branched alkyl group or alkoxy group having 1 to 4 carbon atoms, a nitro group, an acetyl group, or a phenyl group. $R^{111}$ represents a linear, branched or substituted alkyl group, alkenyl group or alkoxyalkyl group having 1 to 8 carbon atoms, a phenyl group, or a naphthyl group, and a part or all of hydrogen atoms of these groups may be further substituted with an alkyl group or alkoxy group having 1 to 4 carbon atoms; a phenyl group that may be substituted with an alkyl group having 1 to 4 carbon atoms or alkoxy group, a nitro group, or an acetyl group; a heteroaromatic group having 3 to 5 carbon atoms; or a chlorine atom or a fluorine atom.

Herein, the arylene group in $R^{110}$ includes a 1,2-phenylene group and a 1,8-naphthylene group. The alkylene group includes a methylene group, an ethylene group, a trimethylene group, a tetramethylene group, a phenylethylene group, and a norbornane-2,3-diyl group. The alkenylene group includes a 1,2-vinylene group, a 1-phenyl-1,2-vinylene group, and a 5-norbornene-2,3-diyl group. The alkyl group in $R^{111}$ includes the same as those in $R^{101a}$ to $R^{101c}$. The alkenyl group includes a vinyl group, a 1-propenyl group, an allyl group, a 1-butenyl group, a 3-butenyl group, an isoprenyl group, a 1-pentenyl group, a 3-pentenyl group, a 4-pentenyl group, a dimethylallyl group, a 1-hexenyl group, a 3-hexenyl group, a 5-hexenyl group, a 1-heptenyl group, a 3-heptenyl group, a 6-heptenyl group, and a 7-octenyl group. The alkoxyalkyl group includes a methoxymethyl group, an ethoxymethyl group, a propoxymethyl group, a butoxymethyl group, a pentyloxymethyl group, a hexyloxymethyl group, a heptyloxymethyl group, a methoxyethyl group, an ethoxyethyl group, a propoxyethyl group, a butoxyethyl group, a pentyloxyethyl group, a hexyloxyethyl group, a methoxypropyl group, an ethoxypropyl group, a propoxypropyl group, a butoxypropyl group, a methoxybutyl group, an ethoxybutyl group, a propoxybutyl group, a methoxypentyl group, an ethoxypentyl group, a methoxyhexyl group, and a methoxyheptyl group.

Herein, the alkyl group having 1 to 4 carbon atoms, which may be further substituted, includes a methyl group, an ethyl group, a propyl group, an isopropyl group, a n-butyl group, a an isobutyl group, and a tert-butyl group. The alkoxy group having 1 to 4 carbon atoms includes a methoxy group, an ethoxy group, a propoxy group, an isopropoxy group, a n-butoxy group, an isobutoxy group, and tert-butoxy group. The phenyl group that may be substituted with an alkyl group or alkoxy group having 1 to 4 carbon atoms, a nitro group, or an acetyl group includes a phenyl group, a tolyl group, a p-tert-butoxyphenyl group, a p-acetylphenyl group, and a p-nitrophenyl group. The heteroaromatic group having 3 to 5 carbon atoms includes a pyridyl group and a furyl group.

Specific examples include onium salts such as tetramethylammonium trifluoromethanesulfonate, tetramethylammonium nonafluorobutanesulfonate, triethylammonium nonafluorobutanesulfonate, pyridinium nonafluorobutanesulfonate, triethylammonium camphorsulfonate, pyridinium camphorsulfonate, tetra n-butylammonium nonafluorobutanesulfonate, tetraphenylammonium nonafluorobutanesulfonate, tetramethylammonium p-toluenesulfonate, diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl) diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris (p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl) sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylene bis[methyl(2-oxocyclopentyl)sulfonium trifluoromethanesulfonate], and 1,2'-naphthylcarbonylmethyltetrahydrothiophenium triflate, diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane, glyoxime derivatives such as bis-(p-toluenesulfonyl)-α-dimethylglyoxime, bis-(p-toluesulfonyl)-α-diphenylglyoxime, bis-(p-toluenesulfonyl)-α-dicyclohexylglyoxime, bis-(p-toluenesulfonyl)-2,3-pentanedioneglyoxime, bis-(p-toluenesulfonyl)-2-methyl-3,4-pentanedioneglyoxime, bis-(n-butanesulfonyl)-α-dimethylglyoxime, bis-(n-butanesulfonyl)-α-diphenylglyoxime, bis-(n-butanesulfonyl)-α-dicyclohexylglyoxime, bis-(n-butanesulfonyl)-2,3-pentanedioneglyoxime, bis-(n-butanesulfonyl)-2-methyl-3,4-pentanedioneglyoxime, bis-(methanesulfonyl)-α-dimethylglyoxime, bis-(trifluoromethanesulfonyl)-α-dimethylglyoxime, bis-(1,1,1-trifluoroethanesulfonyl)-α-dimethylglyoxime, bis-(tert-butanesulfonyl)-α-dimethylglyoxime, bis-(perfluorooctanesulfonyl)-α-dimethylglyoxime, bis-(cyclohexanesulfonyl)-α-dimethylglyoxime, bis-(benzenesulfonyl)-α-dimethylglyoxime, bis-(p-fluorobenzenesulfonyl)-α-dimethylglyoxime, bis-(p-tert-butylbenzenesulfonyl)-α-dimethylglyoxime, bis-(xylenesulfonyl)-α-dimethylglyoxime, and bis-(camphorsulfonyl)-α-dimethylglyoxime, bissulfone derivatives, such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane, β-ketosulfone derivatives such as 2-cyclohexylcarbonyl-2-(p-toluenesulfonyl)propane and 2-isopropylcarbonyl-2-(p-toluenesulfonyl)propane, disulfone derivatives such as a diphenyldisulfone derivative and a dicyclohexyldisulfone derivative, nitrobenzylsulfonate derivatives such as 2,6-dinitrobenzyl p-toluenesulfonate and 2,4-dinitrobenzyl p-toluenesulfonate, sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene, and sulfonic acid ester derivatives of a N-hydroxyimide compound, such as N-hydroxysuccinimide methanesulfonic acid ester, N-hydroxysuccinimide trifluoromethanesulfonic acid ester, N-hydroxysuccinimide ethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide 1-octanesulfonic acid ester, N-hydroxysuccinimide p-toluenesulfonic acid ester, N-hydroxysuccinimide p-methoxybenzenesulfonic acid ester, N-hydroxysuccinimide 2-chloroethanesulfonic acid ester, N-hydroxysuccinimide benzenesulfonic acid ester, N-hydroxysuccinimide-2,4,6-trimethylbenzenesulfonic acid ester, N-hydroxysuccinimide 1-naphthalenesulfonic acid ester, N-hydroxysuccinimide 2-naphthalenesulfonic acid ester, N-hydroxy-2-phenylsuccinimide methanesulfonic acid ester, N-hydroxymaleimide methanesulfonic acid ester, N-hydroxymaleimide ethanesulfonic acid ester, N-hydroxy-2-phenylmaleimide methanesulfonic acid ester, N-hydroxyglutarimide methanesulfonic acid ester, N-hydroxyglutarimide benzenesulfonic acid ester, N-hydroxyphthalimide methanesulfonic acid ester, N-hydroxyphthalimide benzenesulfonic acid ester, N-hydroxyphthalimide trifluoromethanesulfonic acid ester, N-hydroxyphthalimide p-toluenesulfonic acid ester, N-hydroxynaphthalimide methanesulfonic acid ester, N-hydroxynaphthalimide benzenesulfonic acid ester, N-hydroxy-5-norbornene-2,3-dicarboxyimide methanesulfonic acid ester, N-hydroxy-5-norbornene-2,3-dicarboxyimide trifluoromethanesulfonic acid ester, and N-hydroxy-5-norbornene-2,3-dicarboxyimide p-toluenesulfonic acid ester.

Among them, in particular, onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, and 1,2'-naphthylcarbonylmethyltetrahydrothiophenium triflate, diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane, glyoxime derivatives such as bis-(p-toluenesulfonyl)-α-dimethylglyoxime and bis-(n-butanesulfonyl)-α-dimethylglyoxime, bissulfone derivatives such as bisnaphthylsulfonylmethane, and sulfonic acid ester derivatives of an N-hydroxyimide compound, such as N-hydroxysuccinimide methanesulfonic acid ester, N-hydroxysuccinimide trifluoromethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide p-toluenesulfonic acid ester, N-hydroxynaphthalimide methanesulfonic acid ester, and N-hydroxynaphthalimide benzenesulfonic acid ester are preferably used.

In the material for forming an underlayer film for lithography according to the present embodiment, the content of the acid generating agent is not particularly limited, but the content is preferably 0.1 to 50 parts by mass and more preferably 0.5 to 40 parts by mass based on 100 parts by mass of the compound represented by the general formula (1) and the resin having a structure represented by the general formula (2). The content is set within the above range to result in a tendency to increase the acid generation amount to promote a crosslinking reaction, and also to result in a tendency to suppress the occurrence of the mixing phenomenon with a resist layer.

Furthermore, the material for forming an underlayer film for lithography of the present embodiment may contain a basic compound from the viewpoint of improving preservation stability.

The basic compound serves as a quencher to an acid for preventing a trace amount of the acid generated from the acid generating agent from promoting a crosslinking reaction. Examples of such a basic compound include primary, secondary and tertiary aliphatic amines, mixed amines, aromatic amines, heterocyclic amines, a nitrogen-containing compound having a carboxy group, a nitrogen-containing compound having a sulfonyl group, a nitrogen-containing compound having a hydroxyl group, a nitrogen-containing compound having a hydroxyphenyl group, an alcoholic nitrogen-containing compound, an amide derivative, and an imide derivative, but are not particularly limited thereto.

Specifically, specific examples of the primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Specific examples of the secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Specific examples of the tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Specific examples of the mixed amines include dimethylethylamine, methylethylpropylamine, benzylamine, phenethylamine, and benzyldimethylamine. Specific examples of the aromatic amines and heterocyclic amines include aniline derivatives (for example, aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (for example, pyrrole, 2H-pyrrole, 1-methylpyrrole, 2,4-dimethylpyrrole, 2,5-dimethylpyrrole, and N-methylpyrrole), oxazole derivatives (for example, oxazole and isoxazole), thiazole derivatives (for example, thiazole and isothiazole), imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline, 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Furthermore, specific examples of the nitrogen-containing compound having a carboxy group include aminobenzoic acid, indolecarboxylic acid, and amino acid derivatives (for example, nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Specific examples of the nitrogen-containing compound having a sulfonyl group include 3-pyridinesulfonic acid and pyridinium p-toluenesulfonate. Specific examples of the nitrogen-containing compound having a hydroxyl group, the nitrogen-containing compound having a hydroxyphenyl group, and the alcoholic nitrogen-containing compound include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl) morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Specific examples of the amide derivative include formamide, N-methylformamide, N,N-dimethylformamide, acetamide, N-methylacetamide, N,N-dimethylacetamide, propionamide, and benzamide. Specific examples of the imide derivative include phthalimide, succinimide, and maleimide.

In the material for forming an underlayer film for lithography according to the present embodiment, the content of the basic compound is not particularly limited, but the content is preferably 0.001 to 2 parts by mass and more preferably 0.01 to 1 part based on 100 parts by mass of the compound represented by the general formula (1) and the resin having a structure represented by the general formula (2). The content is set within the above preferable range to result in a tendency to improve preservation stability without excessively interrupting a crosslinking reaction.

In addition, the material for forming an underlayer film for lithography of the present embodiment may contain other resins and/or compounds for the purpose of imparting heat curability and controlling absorbance. Such other resins and/or compounds include naphthol resins, xylene resins naphthol-modified resins, phenol-modified resins of naphthalene resins, polyhydroxystyrene, dicyclopentadiene resins, (meth) acrylate, dimethacrylate, trimethacrylate, tetramethacrylate, resins having a naphthalene ring such as vinylnaphthalene and polyacenaphthylene, resins having a biphenyl ring such as phenanthrenequinone and fluorene, resins having a heterocyclic ring having a hetero atom such as thiophene and indene, and resins not containing an aromatic ring; rosin-based resins, and resins or compounds including an alicyclic structure, such as cyclodextrin, adamantane(poly)ol, tricyclodecane(poly)ol and derivatives thereof, but are not particularly limited thereto. Furthermore, the material for forming an underlayer film for lithography of the present embodiment may contain additives known in the art, such as an ultraviolet absorber, a surfactant, a colorant, and a non-ionic surfactant.

The material for forming an underlayer film for lithography according to the present embodiment may contain an organic solvent. As the organic solvent, a known one can be appropriately used as long as it dissolves at least the compound represented by general formula (1) and/or the resin having a structure represented by the general formula (2).

Specific examples of the organic solvent include, for example, ketone-based solvents such as acetone, methyl ethyl ketone, methyl isobutyl ketone, and cyclohexanone, cellosolve-based solvents such as propylene glycol monomethyl ether and propylene glycol monomethyl ether acetate, ester-based solvents such as ethyl lactate, methyl acetate, ethyl acetate, butyl acetate, isoamyl acetate, ethyl lactate, methyl methoxypropionate, and methyl hydroxyisobutyrate, alcohol-based solvents such as methanol, ethanol, isopropanol, and 1-ethoxy-2-propanol, and aromatic hydrocarbons such as toluene, xylene, and anisole, but are not particularly limited thereto. These organic solvents can be used alone, or two or more thereof can be used in combination.

Among the above organic solvents, particularly preferable are cyclohexanone, propylene glycol monomethyl ether, propylene glycol monomethyl ether acetate, ethyl lactate, methyl hydroxyisobutyrate, anisole, in terms of safety.

The content of the organic solvent is not particularly limited, but it is preferably 100 to 10,000 parts by mass and more preferably 200 to 5,000 parts by mass based on 100 parts by mass of the compound represented by the general formula (1) and/or the resin having a structure represented by the general formula (2), from the viewpoint of solubility and film formability.

[Underlayer Film for Lithography and Forming Method of Multilayer Resist Pattern]

An underlayer film for lithography of the present embodiment is formed from the material for forming an underlayer film for lithography.

In addition, a forming method of a multilayer resist pattern of the present embodiment includes forming an underlayer film on a substrate by using the material for forming an underlayer film for lithography, forming at least one photoresist layer on the underlayer film, then irradiating a required region of the photoresist layer with radiation, followed by developing with an alkali.

Furthermore, a forming method of a multilayer resist pattern of the present embodiment includes forming an underlayer film on a substrate by using the material for forming an underlayer film for lithography, forming an intermediate layer film on the underlayer film by using a silicon atom-containing resist intermediate layer film material, forming at least one photoresist layer on the intermediate layer film, then irradiating a required region of the photoresist layer with radiation, followed by developing with an alkali to form a resist pattern, and then etching the intermediate layer film while the resist pattern functions as a mask, etching the underlayer film while the obtained intermediate layer film pattern functions as an etching mask and etching the substrate while the obtained underlayer film pattern functions as an etching mask, to form a pattern on the substrate.

The underlayer film for lithography of the present embodiment is not particularly limited in terms of the forming method thereof as long as it is formed from the material for forming an underlayer film for lithography, and a method known in the art can be applied. For example, the underlayer film can be formed by applying the material for forming an underlayer film for lithography on the substrate by a known coating method or printing method such as spin coating or screen printing, and removing an organic solvent by volatilization or the like. The underlayer film is desirably baked upon forming in order to suppress the occurrence of the mixing phenomenon with an upperlayer resist and also promote a crosslinking reaction. In this case, the baking temperature is not particularly limited, but it is preferably within the range of 80 to 450° C., and more preferably 200 to 400° C. In addition, the baking time is not also particularly limited, but is preferably within the range of 10 to 300 seconds. Herein, the thickness of the underlayer film can be appropriately selected depending on the required properties, and is not particularly limited, but the thickness is usually preferably about 30 to 20,000 nm and more preferably 50 to 15,000 nm.

After the underlayer film is prepared, in the case of a two-layer process, a silicon-containing resist layer or a usual single-layer resist including a hydrocarbon is prepared on the underlayer film, and in the case of a three-layer process, a silicon-containing intermediate layer is prepared on the underlayer film, and a single-layer resist layer not containing silicon is prepared on the silicon-containing intermediate layer. In these cases, a photoresist material for forming the resist layer, which can be used, is a known one.

After the underlayer film is prepared on the substrate, in the case of a two-layer process, a silicon-containing resist layer or a usual single-layer resist including a hydrocarbon can be prepared on the underlayer film, and in the case of a three-layer process, a silicon-containing intermediate layer can be prepared on the underlayer film, and a single-layer resist layer not containing silicon can be prepared on the silicon-containing intermediate layer. In these cases, a photoresist material for forming the resist layer, which can be used, is appropriately selected from known ones, and is not particularly limited.

As the silicon-containing resist material for a two-layer process, a positive-type photoresist material is preferably used, which contains a silicon atom-containing polymer such as a polysilsesquioxane derivative or a vinylsilane derivative used as a base polymer in terms of oxygen gas-etching resistance, and an organic solvent, an acid generating agent and if necessary a basic compound. Herein, as the silicon atom-containing polymer, a known polymer used in such a resist material can be used.

As the silicon-containing intermediate layer for a three-layer process, a polysilsesquioxane-based intermediate layer is preferably used. The intermediate layer is allowed to have an effect as an antireflective film, thereby making it possible to suppress reflection. For example, if a material including many aromatic groups and having a high substrate-etching resistance is used for the underlayer film in a 193 nm exposure process, a k-value tends to be increased to increase substrate reflection, but the reflection can be suppressed by the intermediate layer to thereby make the substrate reflection 0.5% or less. For the intermediate layer having such an antireflection effect, polysilsesquioxane into which a phenyl group or a light-absorbing group having a silicon-silicon bond for 193 nm exposure is introduced and which is to be crosslinked with an acid or heat is preferably used.

An intermediate layer formed by the Chemical Vapour Deposition (CVD) method can also be used. As the intermediate layer having a high effect as an antireflective film, prepared by the CVD method, for example, a SiON film is known. In general, the intermediate layer is formed by a wet process such as a spin coating method or screen printing rather than the CVD method in terms of simplicity and cost effectiveness. Herein, the upperlayer resist in a three-layer process may be of positive-type or negative-type, and the same one as a commonly used single-layer resist can be used therefor.

Furthermore, the underlayer film of the present embodiment can also be used as a usual antireflective film for use in a single-layer resist or a usual underlying material for suppressing pattern collapse. The underlayer film of the present embodiment can also be expected to serve as a hard mask for underlying processing because of being excellent in etching resistance for underlying processing.

In the case where a resist layer is formed by the photoresist material, a wet process such as a spin coating method or screen printing is preferably used as in the case of forming the underlayer film. The resist material is coated by a spin coating method or the like and then usually pre-baked, and such pre-baking is preferably performed in the range of 80 to 180° C. for 10 to 300 seconds. Thereafter, in accordance with an ordinary method, the resultant can be subjected to exposure, post-exposure bake (PEB), and development to obtain a resist pattern. Herein, the thickness of the resist film is not particularly limited, but generally, it is preferably 30 to 500 nm and more preferably 50 to 400 nm.

Light for use in exposure may be appropriately selected depending on the photoresist material to be used. In general, examples thereof include high energy radiation having a wavelength of 300 nm or less, specifically, excimer lasers of 248 nm, 193 nm, and 157 nm, a soft X-ray of 3 to 20 nm, electron beam, and an X-ray.

The resist pattern formed by the above method is a pattern whose collapse is suppressed by the underlayer film of the present embodiment. Therefore, the underlayer film of the present embodiment can be used to thereby obtain a finer pattern, and an exposure amount necessary for obtaining such a resist pattern can be reduced.

Then, the obtained resist pattern is used as a mask to perform etching. As the etching of the underlayer film in a two-layer process, gas etching is preferably used. As the gas etching, etching using oxygen gas is suitable. In addition to oxygen gas, an inert gas such as He and Ar, and CO, $CO_2$, $NH_3$, $SO_2$, $N_2$, $NO_2$, and $H_2$ gases can also be added. The gas etching can also be performed not using oxygen gas but using only CO, $CO_2$, $NH_3$, $N_2$, $NO_2$, and $H_2$ gases. In particular, the latter gases are used for protecting a side wall for preventing a pattern side wall from being undercut. On the other hand, also in the etching of the intermediate layer in a three-layer process, gas etching is preferably used. As the gas etching, the same one as the one described in a two-layer process can be applied. In particular, the intermediate layer is preferably processed in a three-layer process using a fluorocarbon gas with the resist pattern as a mask. Thereafter, as described above, the intermediate layer pattern is used as a mask to perform, for example, oxygen gas etching, thereby processing the underlayer film.

Herein, in the case where an inorganic hard mask intermediate layer film is formed as the intermediate layer, a silicon oxide film, a silicon nitride film, and a silicon oxynitride film (SiON film) are formed by the CVD method, the ALD method, and the like. The method for forming a nitride film is described in, for example, Japanese Patent Laid-Open No. 2002-334869 (Patent Literature 6) and WO2004/066377 (Patent Literature 7).

While the photoresist film can be directly formed on such an intermediate layer film, an organic antireflective film (BARC) may also be formed on the intermediate layer film by spin coating, and the photoresist film may also be formed thereon.

As the intermediate layer, a polysilsesquioxane-based intermediate layer is also preferably used. The resist intermediate layer film is allowed to have an effect as an antireflective film, thereby making it possible to suppress reflection. A material for the polysilsesquioxane-based intermediate layer is described in, for example, specifically, Japanese Patent Laid-Open No. 2007-226170 (Patent Literature 8) and Japanese Patent Laid-Open No. 2007-226204 (Patent Literature 9).

The next etching of the substrate can also be performed by an ordinary method, and, for example, when the substrate is made of $SiO_2$ or SiN, etching with mainly a fluorocarbon gas can be performed, and when the substrate is made of p-Si, Al, or W, etching mainly using a chlorine-based gas or bromine-based gas can be performed. In the case where the substrate is processed by the etching with a fluorocarbon gas, the silicon-containing resist in a two-layer resist process and the silicon-containing intermediate layer in a three-layer process are peeled off at the same time as the processing of the substrate. On the other hand, in the case where the substrate is processed by the etching with a chlorine-based gas or bromine-based gas, the silicon-containing resist layer or the silicon-containing intermediate layer is peeled off separately, and is generally peeled off by dry etching with a fluorocarbon gas after the substrate is processed.

The underlayer film of the present embodiment is characterized by being excellent in etching resistance of such a substrate.

Herein, the substrate that can be used is appropriately selected from ones known in the art, and is not particularly limited, but includes Si, α-Si, p-Si, $SiO_2$, SiN, SiON, W, TiN, and Al substrates. In addition, the substrate may also be a laminate having a processed film (processed substrate) on a base material (support). Such a processed film includes various Low-k films made of Si, $SiO_2$, SiON, SiN, p-Si, α-Si, W, W—Si, Al, Cu, and Al—Si, and stopper films thereof, and a material different from the base material (support) is usually used therefor. Herein, the thickness of the substrate to be processed or the processed film is not particularly limited, but it is usually preferably about 50 to 10,000 nm and more preferably 75 to 5,000 nm.

EXAMPLES

Hereinafter, the present invention will be described by Synthesis Examples and Examples in more detail, but the present invention is not limited thereto at all.

—Carbon Concentration and Oxygen Concentration—

The carbon concentration and the oxygen concentration (% by mass) were measured by organic element analysis.

Apparatus: CHN CORDER MT-6 (manufactured by Yanaco Bunseki Kogyo Co.)

—Molecular Weight—

Measurement was performed by GC-MS analysis using Agilent 5975/6890N manufactured by Agilent. Alternatively, measurement was performed by LC-MS analysis using Acquity UPLC/MALDI-Synapt HDMS manufactured by Water.

—Molecular Weight in Terms of Polystyrene—

Gel permeation chromatography (GPC) analysis was used to determine the weight average molecular weight (Mw) and the number average molecular weight (Mn) in terms of polystyrene, and to determine the degree of dispersion (Mw/Mn).

Apparatus: Shodex GPC-101 type (manufactured by Showa Denko K. K.)

Column: KF-80M×3

Eluent: THF 1 ml/min

Temperature: 40° C.

—Pyrolysis Temperature (Tg)—

An EXSTAR 6000 DSC apparatus manufactured by SII NanoTechnology Inc. was used, and about 5 mg of a sample was placed in an unsealed aluminum container and heated to 500° C. at a rate of temperature rise of 10° C./min in a nitrogen gas (30 ml/min) stream. In this time, a temperature at which a reducing portion appeared on the base line was defined as a pyrolysis temperature (Tg).

—Solubility—

The amount of each compound dissolved in 1-methoxy-2-propanol (PGME) and propylene glycol monomethyl ether acetate (PGMEA) was measured at 23° C., and the results were evaluated according to the following criteria.

Evaluation A: 10% by weight or more

Evaluation B: 3% by weight or more and less than 10% by weight

Evaluation C: less than 3% by weight

Synthesis Example 1

Synthesis of BisN-1

To a container having an inner volume of 100 ml, equipped with a stirrer, a condenser tube and a burette, were charged 1.60 g (10 mmol) of 2,6-naphthalenediol (reagent produced by Sigma-Aldrich Co., LLC.), 1.82 g (10 mmol) of 4-biphenylaldehyde (produced by Mitsubishi Gas Chemical Company, Inc.) and 30 ml of methyl isobutyl ketone, 5 ml of 95% sulfuric acid was added thereto, and a reaction liquid was stirred at 100° C. for 6 hours to perform a reaction. Then, the reaction liquid was concentrated, 50 g of pure water was added thereto to precipitate a reaction product, and the resultant was cooled to room temperature followed by filtration for separation. A solid obtained by filtration was dried, and separated and purified by column chromatography to thereby provide 3.05 g of an objective compound (BisN-1) represented by the following formula.

Herein, the following peaks were observed by 400 MHz-$^1$H-NMR, and it was confirmed that the compound had a chemical structure of the following formula. In addition, it was confirmed from a doublet signal of protons at 3- and 4-positions that 2,6-dihydroxynaphthol was substituted at 1-position.

$^1$H-NMR: (d-DMSO, Internal reference TMS)

δ (ppm) 9.7 (2H, O—H), 7.2-8.5 (19H, Ph-H), 6.6 (1H, C—H)

[Formula 26]

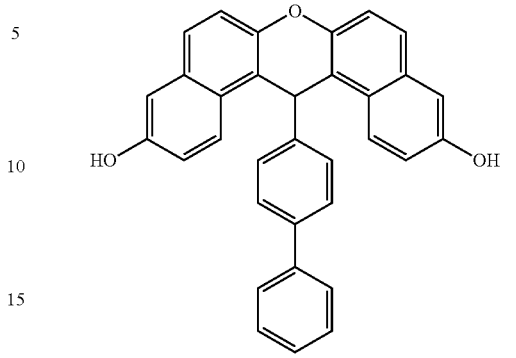

(BisN-1)

As a result of organic element analysis, the carbon concentration and the oxygen concentration of the resulting compound (BisN-1) were 84.5% and 10.3%, respectively. The carbon content rate is high and the oxygen content rate is low, and it is thus found that the etching resistance is high.

The molecular weight of the resulting compound was measured by the above method, and as a result, it was 464.

As a result of thermogravimetric measurement (TG), the pyrolysis temperature of the resulting compound (BisN-1) was 410° C. The compound has a high heat resistance, and can be applied to high-temperature baking.

The solubility in PGME and PGMEA was 20% by weight or more, and was excellent (Evaluation A). Therefore, the compound can be expected to have a high preservation stability in a solution state and applicability to an edge bead rinse liquid (mixed liquid of PGME/PGMEA) widely used in a semiconductor microfabrication process.

Synthesis Example 2

Synthesis of BisN-2

Except that 3.20 g (20 mmol) of 2,7-naphthalenediol (reagent produced by Sigma-Aldrich Co., LLC.) was used instead of 3.20 g (20 mmol) of 2,6-naphthalenediol, the same manner as in Synthesis Example 1 was performed to thereby provide 0.2 g of an objective compound (BisN-2) represented by the following formula.

As a result of organic element analysis, the carbon concentration and the oxygen concentration of the resulting compound (BisN-2) were 84.5% and 10.3%, respectively. The carbon content rate is high and the oxygen content rate is low, and it is thus found that the etching resistance is high.

The molecular weight of the resulting compound was measured by the above method, and as a result, it was 464.

NMR measurement of the resulting compound was performed under the above measurement conditions, and the following peaks were observed. It was confirmed that the compound had a chemical structure of the following formula.

δ (ppm) 9.7 (2H, O—H), 7.2-8.5 (19H, Ph-H), 6.6 (1H, C—H)

As a result of thermogravimetric measurement (TG), the pyrolysis temperature of the resulting compound (BisN-2) was 410° C. The compound has a high heat resistance, and can be applied to high-temperature baking.

The solubility in PGME and PGMEA was 3% by weight or more and less than 20% by weight, and was good (Evaluation B). Therefore, the compound can be expected to have a high preservation stability in a solution state and applicability to an edge bead rinse liquid (mixed liquid of PGME/PGMEA) widely used in a semiconductor microfabrication process.

[Formula 27]

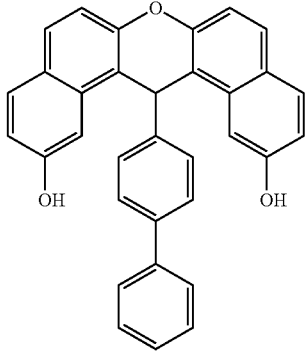

(BisN-2)

[Formula 28]

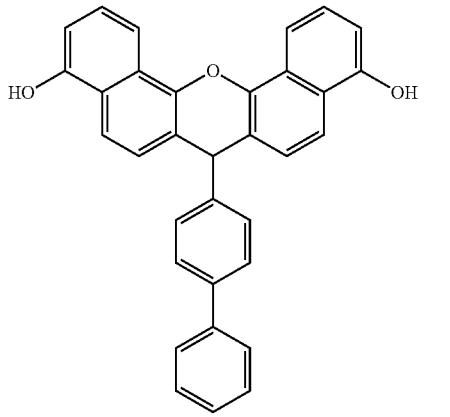

(BisN-3)

Synthesis Example 3

Synthesis of BisN-3

Except that 3.20 g (20 mmol) of 1,5-naphthalenediol (reagent produced by Sigma-Aldrich Co., LLC.) was used instead of 3.20 g (20 mmol) of 2,6-naphthalenediol, the same manner as in Synthesis Example 1 was performed to thereby provide 0.2 g of an objective compound (BisN-3) represented by the following formula.

As a result of organic element analysis, the carbon concentration and the oxygen concentration of the resulting compound (BisN-3) were 84.5% and 10.3%, respectively. The carbon content rate is high and the oxygen content rate is low, and it is thus found that the etching resistance is high.

The molecular weight of the resulting compound was measured by the above method, and as a result, it was 464.

NMR measurement of the resulting compound was performed under the above measurement conditions, and the following peaks were observed. It was confirmed that the compound had a chemical structure of the following formula.

δ (ppm) 9.7 (2H, O—H), 7.2-8.5 (19H, Ph-H), 6.6 (1H, C—H)

As a result of thermogravimetric measurement (TG), the pyrolysis temperature of the resulting compound (BisN-3) was 410° C. The compound has a high heat resistance, and can be applied to high-temperature baking.

The solubility in PGME and PGMEA was 3% by weight or more and less than 20% by weight, and was good (Evaluation B). Therefore, the compound can be expected to have a high preservation stability in a solution state and applicability to an edge bead rinse liquid (mixed liquid of PGME/PGMEA) widely used in a semiconductor microfabrication process.

Synthesis Example 4

Synthesis of BisN-4

Except that 3.20 g (20 mmol) of 1,6-naphthalenediol (reagent produced by Sigma-Aldrich Co., LLC.) was used instead of 3.20 g (20 mmol) of 2,6-naphthalenediol, the same manner as in Synthesis Example 1 was performed to thereby provide 0.2 g of an objective compound (BisN-4) represented by the following formula.

As a result of organic element analysis, the carbon concentration and the oxygen concentration of the resulting compound (BisN-4) were 84.5% and 10.3%, respectively. The carbon content rate is high and the oxygen content rate is low, and it is thus found that the etching resistance is high.

The molecular weight of the resulting compound was measured by the above method, and as a result, it was 464.

NMR measurement of the resulting compound was performed under the above measurement conditions, and the following peaks were observed. It was confirmed that the compound had a chemical structure of the following formula.

δ (ppm) 9.7 (2H, O—H), 7.2-8.5 (19H, Ph-H), 6.6 (1H, C—H)

As a result of thermogravimetric measurement (TG), the pyrolysis temperature of the resulting compound (BisN-4) was 410° C. The compound has a high heat resistance, and can be applied to high-temperature baking.

The solubility in PGME and PGMEA was 3% by weight or more and less than 20% by weight, and was good (Evaluation B). Therefore, the compound can be expected to have a high preservation stability in a solution state and applicability to an edge bead rinse liquid (mixed liquid of PGME/PGMEA) widely used in a semiconductor microfabrication process.

[Formula 29]

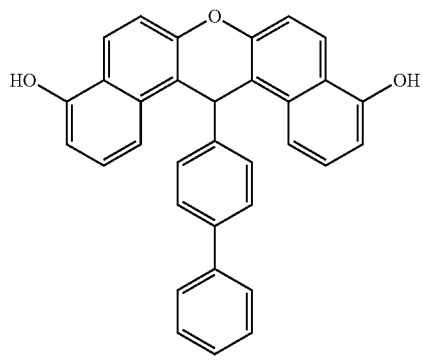

(BisN-4)

Synthesis Example 5

Synthesis of BisN-5

Except that 3.20 g (20 mmol) of 1,7-naphthalenediol (reagent produced by Sigma-Aldrich Co., LLC.) was used instead of 3.20 g (20 mmol) of 2,6-naphthalenediol, the same manner as in Synthesis Example 1 was performed to thereby provide 0.2 g of an objective compound (BisN-5) represented by the following formula.

As a result of organic element analysis, the carbon concentration and the oxygen concentration of the resulting compound (BisN-5) were 84.5% and 10.3%, respectively. The carbon content rate is high and the oxygen content rate is low, and it is thus found that the etching resistance is high.

The molecular weight of the resulting compound was measured by the above method, and as a result, it was 464.

NMR measurement of the resulting compound was performed under the above measurement conditions, and the following peaks were observed. It was confirmed that the compound had a chemical structure of the following formula.

δ (ppm) 9.7 (2H, O—H), 7.2-8.5 (19H, Ph-H), 6.6 (1H, C—H)

As a result of thermogravimetric measurement (TG), the pyrolysis temperature of the resulting compound (BisN-5) was 410° C. The compound has a high heat resistance, and can be applied to high-temperature baking.

The solubility in PGME and PGMEA was 3% by weight or more and less than 20% by weight, and was good (Evaluation B). Therefore, the compound can be expected to have a high preservation stability in a solution state and applicability to an edge bead rinse liquid (mixed liquid of PGME/PGMEA) widely used in a semiconductor microfabrication process.

[Formula 30]

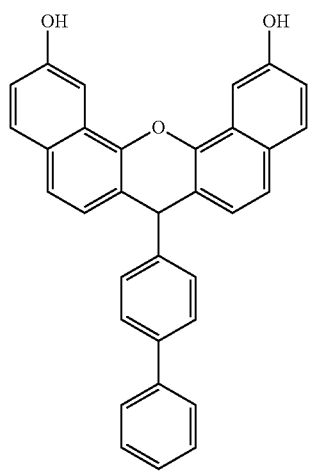

(BisN-5)

Synthesis Example 6

Synthesis of BisN-6

Except that 3.20 g (20 mmol) of 2,3-naphthalenediol (reagent produced by Sigma-Aldrich Co., LLC.) was used instead of 3.20 g (20 mmol) of 2,6-naphthalenediol, the same manner as in Synthesis Example 1 was performed to thereby provide 0.2 g of an objective compound (BisN-6) represented by the following formula.

As a result of organic element analysis, the carbon concentration and the oxygen concentration of the resulting compound (BisN-6) were 84.5% and 10.3%, respectively. The carbon content rate is high and the oxygen content rate is low, and it is thus found that the etching resistance is high.

The molecular weight of the resulting compound was measured by the above method, and as a result, it was 464.

NMR measurement of the resulting compound was performed under the above measurement conditions, and the following peaks were observed. It was confirmed that the compound had a chemical structure of the following formula.

δ (ppm) 9.7 (2H, O—H), 7.2-8.5 (19H, Ph-H), 6.6 (1H, C—H)

As a result of thermogravimetric measurement (TG), the pyrolysis temperature of the resulting compound (BisN-6) was 410° C. The compound has a high heat resistance, and can be applied to high-temperature baking.

The solubility in PGME and PGMEA was 3% by weight or more and less than 20% by weight, and was good (Evaluation B). Therefore, the compound can be expected to have a high preservation stability in a solution state and applicability to an edge bead rinse liquid (mixed liquid of PGME/PGMEA) widely used in a semiconductor microfabrication process.

[Formula 31]

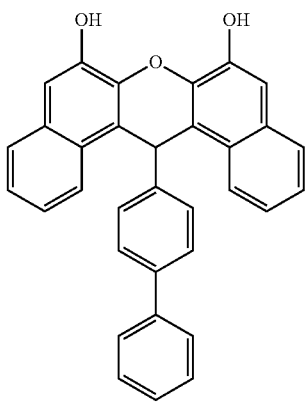

(BisN-6)

Synthesis Example 7

Synthesis of BisN-7

Except that 1.56 g (10 mmol) of 1-naphthaldehyde (reagent produced by Sigma-Aldrich Co., LLC.) was used instead of 1.82 g (10 mmol) of 4-biphenylcarboxaldehyde (produced by Mitsubishi Gas Chemical Company, Inc.), the same manner as in Synthesis Example 1 was performed to thereby provide 0.2 g of an objective compound (BisN-7) represented by the following formula.

As a result of organic element analysis, the carbon concentration and the oxygen concentration of the resulting compound (BisN-7) were 84.5% and 10.9%, respectively. The carbon content rate is high and the oxygen content rate is low, and it is thus found that the etching resistance is high.

The molecular weight of the resulting compound was measured by the above method, and as a result, it was 440.

NMR measurement of the resulting compound was performed under the above measurement conditions, and the following peaks were observed. It was confirmed that the compound had a chemical structure of the following formula.

δ (ppm) 9.7 (2H, O—H), 7.2-8.5 (17H, Ph-H), 6.6 (1H, C—H)

As a result of thermogravimetric measurement (TG), the pyrolysis temperature of the resulting compound (BisN-7) was 415° C. The compound has a high heat resistance, and can be applied to high-temperature baking.

The solubility in PGME and PGMEA was 3% by weight or more and less than 20% by weight, and was good (Evaluation B). Therefore, the compound can be expected to have a high preservation stability in a solution state and applicability to an edge bead rinse liquid (mixed liquid of PGME/PGMEA) widely used in a semiconductor microfabrication process.

[Formula 32]

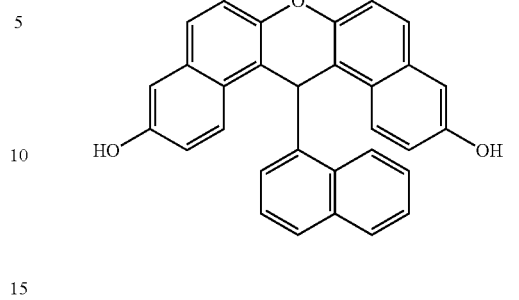

(BisN-7)

Synthesis Example 8

Synthesis of BisN-8

Except that 2.06 g (10 mmol) of 9-phenanthrenealdehyde (reagent produced by Wako Pure Chemical Industries, Ltd.) was used instead of 1.82 g (10 mmol) of 4-biphenylcarboxaldehyde (produced by Mitsubishi Gas Chemical Company, Inc.), the same manner as in Synthesis Example 1 was performed to thereby provide 0.2 g of an objective compound (BisN-8) represented by the following formula.

As a result of organic element analysis, the carbon concentration and the oxygen concentration of the resulting compound (BisN-8) were 85.7% and 9.8%, respectively. The carbon content rate is high and the oxygen content rate is low, and it is thus found that the etching resistance is high.

The molecular weight of the resulting compound was measured by the above method, and as a result, it was 490.

NMR measurement of the resulting compound was performed under the above measurement conditions, and the following peaks were observed. It was confirmed that the compound had a chemical structure of the following formula.

δ (ppm) 9.7 (2H, O—H), 7.2-8.5 (19H, Ph-H), 6.6 (1H, C—H)

As a result of thermogravimetric measurement (TG), the pyrolysis temperature of the resulting compound (BisN-8) was 415° C. The compound has a high heat resistance, and can be applied to high-temperature baking.

The solubility in PGME and PGMEA was 3% by weight or more and less than 20% by weight, and was good (Evaluation B). Therefore, the compound can be expected to have a high preservation stability in a solution state and applicability to an edge bead rinse liquid (mixed liquid of PGME/PGMEA) widely used in a semiconductor microfabrication process.

[Formula 33]

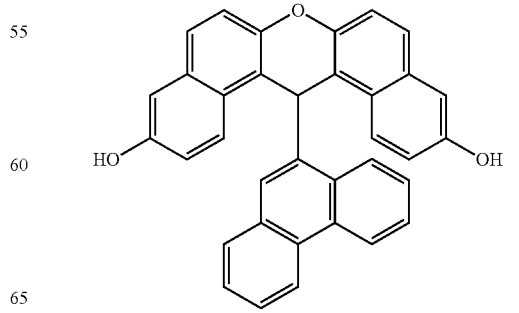

(BisN-8)

Synthesis Example 9

Synthesis of BisN-9

Except that 2.30 g (10 mmol) of 1-pyrenealdehyde (reagent produced by Sigma-Aldrich Co., LLC.) was used instead of 1.82 g (10 mmol) of 4-biphenylcarboxaldehyde (produced by Mitsubishi Gas Chemical Company, Inc.), the same manner as in Synthesis Example 1 was performed to thereby provide 0.2 g of an objective compound (BisN-9) represented by the following formula.

As a result of organic element analysis, the carbon concentration and the oxygen concentration of the resulting compound (BisN-9) were 86.4% and 9.3%, respectively. The carbon content rate is high and the oxygen content rate is low, and it is thus found that the etching resistance is high.

The molecular weight of the resulting compound was measured by the above method, and as a result, it was 514.

NMR measurement of the resulting compound was performed under the above measurement conditions, and the following peaks were observed. It was confirmed that the compound had a chemical structure of the following formula.

δ (ppm) 9.7 (2H, O—H), 7.2-8.5 (19H, Ph-H), 6.6 (1H, C—H)

As a result of thermogravimetric measurement (TG), the pyrolysis temperature of the resulting compound (BisN-9) was 420° C. The compound has a high heat resistance, and can be applied to high-temperature baking.

The solubility in PGME and PGMEA was 3% by weight or more and less than 20% by weight, and was good (Evaluation B). Therefore, the compound can be expected to have a high preservation stability in a solution state and applicability to an edge bead rinse liquid (mixed liquid of PGME/PGMEA) widely used in a semiconductor microfabrication process.

[Formula 34]

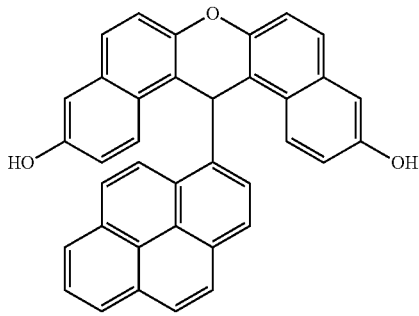

(BisN-9)

Synthesis Example 10

Synthesis of BisN-10

Except that 0.98 g (10 mmol) of cyclohexanone (reagent produced by Sigma-Aldrich Co., LLC.) was used instead of 1.82 g (10 mmol) of 4-biphenylcarboxaldehyde (produced by Mitsubishi Gas Chemical Company, Inc.), the same manner as in Synthesis Example 1 was performed to thereby provide 0.2 g of an objective compound (BisN-10) represented by the following formula.

As a result of organic element analysis, the carbon concentration and the oxygen concentration of the resulting compound (BisN-10) were 81.7% and 12.6%, respectively. The carbon content rate is high and the oxygen content rate is low, and it is thus found that the etching resistance is high.

The molecular weight of the resulting compound was measured by the above method, and as a result, it was 382.

NMR measurement of the resulting compound was performed under the above measurement conditions, and the following peaks were observed. It was confirmed that the compound had a chemical structure of the following formula.

δ (ppm) 9.7 (2H, O—H), 7.2-8.5 (10H, Ph-H), 2.1-2.5 (10H, C—H)

As a result of thermogravimetric measurement (TG), the pyrolysis temperature of the resulting compound (BisN-10) was 400° C. The compound has a high heat resistance, and can be applied to high-temperature baking.

The solubility in PGME and PGMEA was 3% by weight or more and less than 20% by weight, and was good (Evaluation B). Therefore, the compound can be expected to have a high preservation stability in a solution state and applicability to an edge bead rinse liquid (mixed liquid of PGME/PGMEA) widely used in a semiconductor microfabrication process.

[Formula 35]

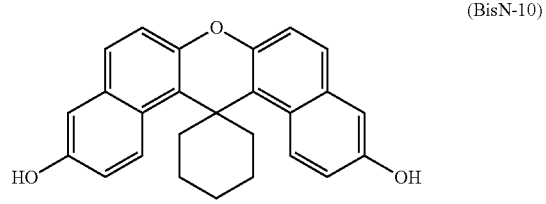

(BisN-10)

Synthesis Example 11

Synthesis of BisN-11

Except that 1.80 g (10 mmol) of 9-fluorenone (reagent produced by Sigma-Aldrich Co., LLC.) was used instead of 1.82 g (10 mmol) of 4-biphenylcarboxaldehyde (produced by Mitsubishi Gas Chemical Company, Inc.), the same manner as in Synthesis Example 1 was performed to thereby provide 0.2 g of an objective compound (BisN-11) represented by the following formula.

As a result of organic element analysis, the carbon concentration and the oxygen concentration of the resulting compound (BisN-11) were 85.3% and 10.3%, respectively. The carbon content rate is high and the oxygen content rate is low, and it is thus found that the etching resistance is high.

The molecular weight of the resulting compound was measured by the above method, and as a result, it was 464.

NMR measurement of the resulting compound was performed under the above measurement conditions, and the following peaks were observed. It was confirmed that the compound had a chemical structure of the following formula.

δ (ppm) 9.7 (2H, O—H), 7.2-8.5 (18H, Ph-H)

As a result of thermogravimetric measurement (TG), the pyrolysis temperature of the resulting compound (BisN-11) was 450° C. The compound has a high heat resistance, and can be applied to high-temperature baking.

The solubility in PGME and PGMEA was 3% by weight or more and less than 20% by weight, and was good (Evaluation B). Therefore, the compound can be expected to have a high preservation stability in a solution state and applicability to an edge bead rinse liquid (mixed liquid of PGME/PGMEA) widely used in a semiconductor microfabrication process.

[Formula 36]

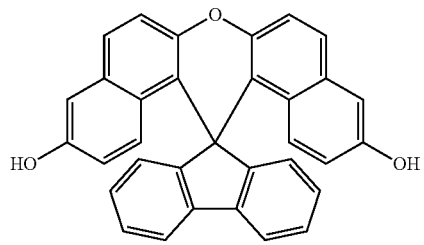

(BisN-11)

Synthesis Example 12

Synthesis of BisN-12

Except that 0.67 g (5 mmol) of terephthalaldehyde (reagent produced by Sigma-Aldrich Co., LLC.) was used instead of 1.82 g (10 mmol) of 4-biphenylcarboxaldehyde (produced by Mitsubishi Gas Chemical Company, Inc.), the same manner as in Synthesis Example 1 was performed to thereby provide 0.1 g of an objective compound (BisN-12) represented by the following formula.

As a result of organic element analysis, the carbon concentration and the oxygen concentration of the resulting compound (BisN-12) were 82.0% and 13.7%, respectively. The carbon content rate is high and the oxygen content rate is low, and it is thus found that the etching resistance is high.

The molecular weight of the resulting compound was measured by the above method, and as a result, it was 702.

NMR measurement of the resulting compound was performed under the above measurement conditions, and the following peaks were observed. It was confirmed that the compound had a chemical structure of the following formula.

δ (ppm) 9.7 (4H, O—H), 7.2-8.5 (24H, Ph-H), 6.6 (2H, C—H)

As a result of thermogravimetric measurement (TG), the pyrolysis temperature of the resulting compound (BisN-12) was 410° C. The compound has a high heat resistance, and can be applied to high-temperature baking.

The solubility in PGME and PGMEA was 3% by weight or more and less than 20% by weight, and was good (Evaluation B). Therefore, the compound can be expected to have a high preservation stability in a solution state and applicability to an edge bead rinse liquid (mixed liquid of PGME/PGMEA) widely used in a semiconductor microfabrication process.

[Formula 37]

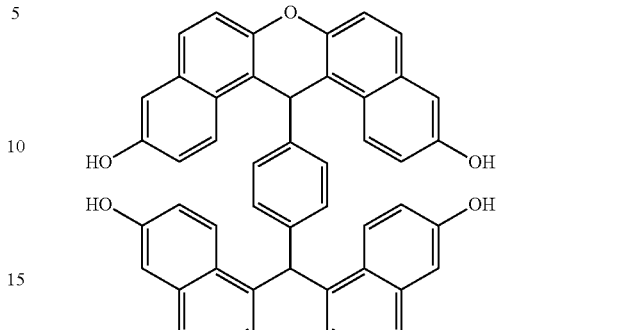

(BisN-12)

Synthesis Example 13

Synthesis of BisN-13

Except that 1.05 g (5 mmol) of 4,4'-diformylbiphenyl (reagent produced by Sigma-Aldrich Co., LLC.) was used instead of 1.82 g (10 mmol) of 4-biphenylcarboxaldehyde (produced by Mitsubishi Gas Chemical Company, Inc.), the same manner as in Synthesis Example 1 was performed to thereby provide 0.1 g of an objective compound (BisN-13) represented by the following formula.

As a result of organic element analysis, the carbon concentration and the oxygen concentration of the resulting compound (BisN-13) were 83.3% and 12.3%, respectively. The carbon content rate is high and the oxygen content rate is low, and it is thus found that the etching resistance is high.

The molecular weight of the resulting compound was measured by the above method, and as a result, it was 778.

NMR measurement of the resulting compound was performed under the above measurement conditions, and the following peaks were observed. It was confirmed that the compound had a chemical structure of the following formula.

δ (ppm) 9.7 (4H, O—H), 7.2-8.5 (28H, Ph-H), 6.6 (2H, C—H)

As a result of thermogravimetric measurement (TG), the pyrolysis temperature of the resulting compound (BisN-13) was 410° C. The compound has a high heat resistance, and can be applied to high-temperature baking.

The solubility in PGME and PGMEA was 3% by weight or more and less than 20% by weight, and was good (Evaluation B). Therefore, the compound can be expected to have a high preservation stability in a solution state and applicability to an edge bead rinse liquid (mixed liquid of PGME/PGMEA) widely used in a semiconductor microfabrication process.

[Formula 38]

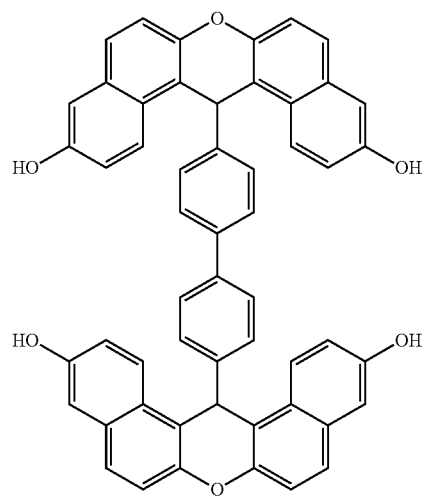

(BisN-13)

[Formula 39]

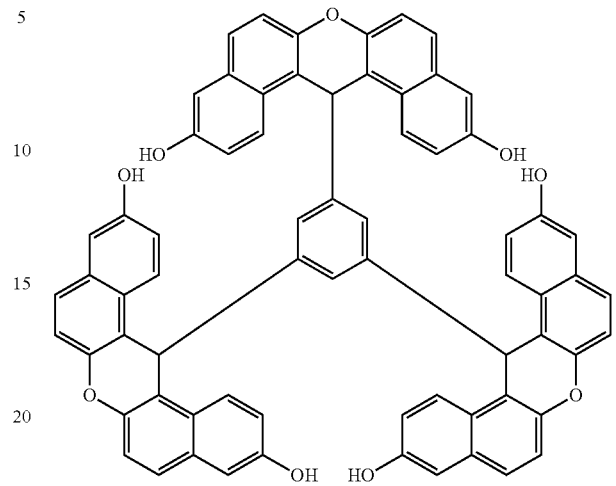

(BisN-14)

Synthesis Example 14

Synthesis of BisN-14

Except that 0.53 g (3.3 mmol) of 1,3,5-benzenetricarbaldehyde (reagent produced by Mitsubishi Gas Chemical Company, Inc.) was used instead of 1.82 g (10 mmol) of 4-biphenylcarboxaldehyde (produced by Mitsubishi Gas Chemical Company, Inc.), the same manner as in Synthesis Example 1 was performed to thereby provide 0.1 g of an objective compound (BisN-14) represented by the following formula.

As a result of organic element analysis, the carbon concentration and the oxygen concentration of the resulting compound (BisN-14) were 81.6% and 14.2%, respectively. The carbon content rate is high and the oxygen content rate is low, and it is thus found that the etching resistance is high.

The molecular weight of the resulting compound was measured by the above method, and as a result, it was 1014.

NMR measurement of the resulting compound was performed under the above measurement conditions, and the following peaks were observed. It was confirmed that the compound had a chemical structure of the following formula.

δ (ppm) 9.7 (6H, O—H), 7.2-8.5 (33H, Ph-H), 6.6 (3H, C—H)

As a result of thermogravimetric measurement (TG), the pyrolysis temperature of the resulting compound (BisN-14) was 410° C. The compound has a high heat resistance, and can be applied to high-temperature baking.

The solubility in PGME and PGMEA was 3% by weight or more and less than 20% by weight, and was good (Evaluation B). Therefore, the compound can be expected to have a high preservation stability in a solution state and applicability to an edge bead rinse liquid (mixed liquid of PGME/PGMEA) widely used in a semiconductor microfabrication process.

Synthesis Example 15

Synthesis of RBisN-1

To a container having an inner volume of 100 ml, equipped with a stirrer, a condenser tube and a burette, were charged 10 g (21 mmol) of BisN-1, 0.7 g (42 mmol) of paraformaldehyde, 50 ml of glacial acetic acid and 50 ml of PGME, 8 ml of 95% sulfuric acid was added thereto, and a reaction liquid was stirred at 100° C. for 6 hours to perform a reaction. Then, the reaction liquid was concentrated, 1000 ml of methanol was added thereto to precipitate a reaction product, and the resultant was cooled to room temperature followed by filtration for separation. A solid obtained by filtration was dried, and separated and purified by column chromatography to thereby provide 7.2 g of an objective resin (RBisN-1) having a structure represented by the following formula.

As a result of organic element analysis, the carbon concentration and the oxygen concentration of the resulting resin (RBisN-1) were 85.0% and 10.0%, respectively. The carbon content rate is high and the oxygen content rate is low, and it is thus found that the etching resistance is high.

The molecular weight in terms of polystyrene with respect to the resulting resin was measured by the above method, and as a result, Mn was 778, Mw was 1793 and Mw/Mn was 2.30.

NMR measurement of the resulting resin was performed under the above measurement conditions, and the following peaks were observed. It was confirmed that the resin had a chemical structure of the following formula.

δ (ppm) 9.7 (2H, O—H), 7.2-8.5 (17H, Ph-H), 6.6 (1H, C—H), 4.1 (2H, —CH$_2$)

As a result of thermogravimetric measurement (TG), the pyrolysis temperature of the resulting resin (RBisN-1) was 405° C. The resin has a high heat resistance, and can be applied to high-temperature baking.

The solubility in PGME and PGMEA was 3% by weight or more and less than 20% by weight, and was good (Evaluation B). Therefore, the resin can be expected to have a high preservation stability in a solution state and applicability to an edge bead rinse liquid (mixed liquid of PGME/PGMEA) widely used in a semiconductor microfabrication process.

[Formula 40]

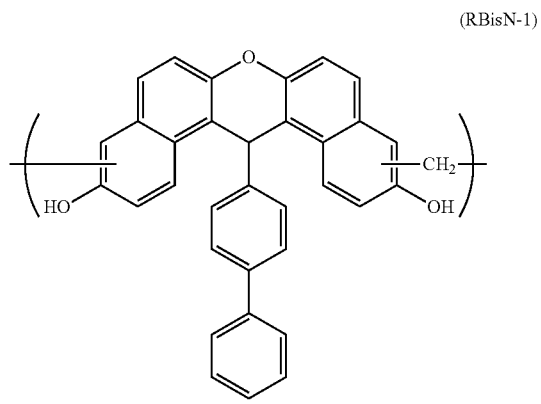

(RBisN-1)

Synthesis Example 16

Synthesis of RBisN-2

Except that 7.6 g (42 mmol) of 4-biphenylcarboxaldehyde (produced by Mitsubishi Gas Chemical Company, Inc.) was used instead of 0.7 g (42 mmol) of paraformaldehyde, the same manner as in Synthesis Example 15 was performed to thereby provide 7.6 g of an objective resin (RBisN-2) having a structure represented by the following formula.

As a result of organic element analysis, the carbon concentration and the oxygen concentration of the resulting resin (RBisN-2) were 87.6% and 7.6%, respectively. The carbon content rate is high and the oxygen content rate is low, and it is thus found that the etching resistance is high.

The molecular weight in terms of polystyrene with respect to the resulting resin was measured by the above method, and as a result, Mn was 562, Mw was 1168 and Mw/Mn was 2.08.

NMR measurement of the resulting resin was performed under the above measurement conditions, and the following peaks were observed. It was confirmed that the resin had a chemical structure of the following formula.

δ (ppm) 9.7 (2H, O—H), 7.2-8.8 (26H, Ph-H), 6.6 (1H, C—H), 4.5 (1H, —CH$_2$)

As a result of thermogravimetric measurement (TG), the pyrolysis temperature of the resulting resin (RBisN-2) was 405° C. The resin has a high heat resistance, and can be applied to high-temperature baking.

The solubility in PGME and PGMEA was 3% by weight or more and less than 20% by weight, and was good (Evaluation B). Therefore, the resin can be expected to have a high preservation stability in a solution state and applicability to an edge bead rinse liquid (mixed liquid of PGME/PGMEA) widely used in a semiconductor microfabrication process.

[Formula 41]

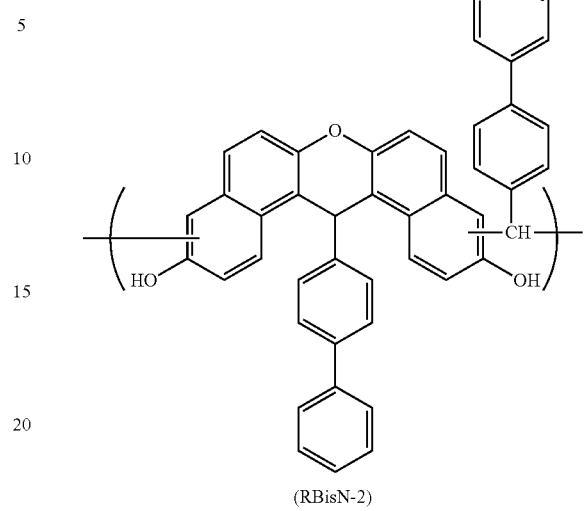

(RBisN-2)

Production Example 1

To a four-neck flask having a bottom outlet and an inner volume of 10 L, equipped with a Dimroth condenser tube, a thermometer and a stirring blade, were charged 1.09 kg (7 mol, produced by Mitsubishi Gas Chemical Company, Inc.) of 1,5-dimethylnaphthalene, 2.1 kg (28 mol as formaldehyde, produced by Mitsubishi Gas Chemical Company, Inc.) of a 40% by mass aqueous formalin solution and 0.97 ml of 98% by mass sulfuric acid (produced by Kanto Chemical Co., Inc.) under a nitrogen stream, and allowed the reaction to run under ordinary pressure for 7 hours with refluxing at 100° C. Thereafter, ethylbenzene (special grade chemical, produced by Wako Pure Chemical Industries, Ltd.) (1.8 kg) as a dilution solvent was added to the reaction solution and left to stand, and then an aqueous phase being a bottom phase was removed. Furthermore, the resultant was neutralized and washed with water, and ethylbenzene and the unreacted 1,5-dimethylnaphthalene were distilled off under reduced pressure, thereby providing 1.25 kg of a dimethylnaphthalene formaldehyde resin as a light-brown solid.

With respect to the molecular weight of the resulting dimethylnaphthalene formaldehyde, Mn was 562, Mw was 1168 and Mw/Mn was 2.08. In addition, the carbon concentration was 84.2% by mass, and the oxygen concentration was 8.3% by mass.

Thereafter, to a four-neck flask having an inner volume of 0.5 L, equipped with a Dimroth condenser tube, a thermometer and a stirring blade, were charged 100 g (0.51 mol) of the dimethylnaphthalene formaldehyde resin obtained in Production Example 1 and 0.05 g of paratoluenesulfonic acid under a nitrogen stream, heated for 2 hours with the temperature being raised to 190° C., and then stirred. Thereafter, 52.0 g (0.36 mol) of 1-naphthol was further added thereto, and further heated to 220° C. to allow the reaction to run for 2 hours. After being diluted with a solvent, the resultant was neutralized and washed with water, and the solvent was removed under reduced pressure to thereby provide 126.1 g of a modified resin (CR-1) as a blackish brown solid.

With respect to the resulting resin (CR-1), Mn was 885, Mw was 2220 and Mw/Mn was 4.17. In addition, the carbon concentration was 89.1% by mass and the oxygen concentration was 4.5% by mass.

Examples 1 to 16, Comparative Example 1

Each material for forming an underlayer film for lithography, having each composition shown in Table 1, was prepared. Then, such a material for forming an underlayer film was spin-coated on a silicon substrate, thereafter baked at 240° C. for 60 seconds and further at 400° C. for 120 seconds to prepare each underlayer film having a film thickness of 200 nm.

An etching test was performed under conditions shown below to evaluate etching resistance. The evaluation results are shown in Table 1.

[Etching Test]
Etching apparatus: RIE-10NR manufactured by Samco Inc.
Output: 50 W
Pressure: 20 Pa
Time: 2 min
Etching Gas
Ar gas flow rate:$CF_4$ gas flow rate:$O_2$ gas flow rate=50:5:5 (sccm)

[Evaluation of Etching Resistance]
The evaluation of etching resistance was performed according to the following procedure.

First, an underlayer film of novolac was prepared under the same conditions as those in Example 1 except that novolac (PSM4357 produced by Gunei Chemical Industry Co., Ltd.) was used instead of the compound (BisN-1) of Example 1. Then, the underlayer film of novolac was subjected to the etching test, and the etching rate in that time was measured.

Then, the underlayer films of Examples 1 to 16 and Comparative Example 1 were subjected to the etching test in the same manner, and the etching rates were measured.

Then, the etching resistances were evaluated according to the following criteria based on the etching rate of the underlayer film of novolac.

<Evaluation Criteria>
A; etching rate of less than −10% compared with the underlayer film of novolac
B; etching rate of −10% to +5% compared with underlayer film of novolac
C; etching rate of more than +5% compared with the underlayer film of novolac

TABLE 1

| | Compound or Resin (parts by mass) | Organic solvent (parts by mass) | Acid generating agent (parts by mass) | Cross-linking agent (parts by mass) | Evaluation of etching resistance |
|---|---|---|---|---|---|
| Example 1 | BisN-1 (10) | CHN (90) | DTDPI (0.5) | Nikalac (0.5) | A |
| Example 2 | BisN-2 (10) | CHN (90) | DTDPI (0.5) | Nikalac (0.5) | A |
| Example 3 | BisN-3 (10) | CHN (90) | DTDPI (0.5) | Nikalac (0.5) | A |
| Example 4 | BisN-4 (10) | CHN (90) | DTDPI (0.5) | Nikalac (0.5) | A |
| Example 5 | BisN-5 (10) | CHN (90) | DTDPI (0.5) | Nikalac (0.5) | A |
| Example 6 | BisN-6 (10) | CHN (90) | DTDPI (0.5) | Nikalac (0.5) | A |
| Example 7 | BisN-7 (10) | CHN (90) | DTDPI (0.5) | Nikalac (0.5) | A |
| Example 8 | BisN-8 (10) | CHN (90) | DTDPI (0.5) | Nikalac (0.5) | A |
| Example 9 | BisN-9 (10) | CHN (90) | DTDPI (0.5) | Nikalac (0.5) | A |
| Example 10 | BisN-10 (10) | CHN (90) | DTDPI (0.5) | Nikalac (0.5) | A |
| Example 11 | BisN-11 (10) | CHN (90) | DTDPI (0.5) | Nikalac (0.5) | A |
| Example 12 | BisN-12 (10) | CHN (90) | DTDPI (0.5) | Nikalac (0.5) | A |
| Example 13 | BisN-13 (10) | CHN (90) | DTDPI (0.5) | Nikalac (0.5) | A |
| Example 14 | BisN-14 (10) | CHN (90) | DTDPI (0.5) | Nikalac (0.5) | A |
| Example 15 | RBisN-1 (10) | CHN (90) | DTDPI (0.5) | Nikalac (0.5) | A |
| Example 16 | RBisN-2 (10) | CHN (90) | DTDPI (0.5) | Nikalac (0.5) | A |
| Comparative Example 1 | CR-1 (10) | CHN (90) | DTDPI (0.5) | Nikalac (0.5) | C |

Acid generating agent: di-tert-butyldiphenyliodonium nonafluoromethanesulfonate (DTDPI) produced by Midori Kagaku Co., Ltd.
Crosslinking agent: Nikalac MX270 (Nikalac) produced by Sanwa Chemical Co., Ltd.
Organic solvent: cyclohexanone (CHN)
Novolac: PSM4357 produced by Gunei Chemical Industry Co., Ltd.

Examples 17 to 32, Comparative Example 2

Then, the solution of the material for forming an underlayer film for lithography in each of Examples 1 to 16 was coated on a $SiO_2$ substrate having a film thickness of 300 nm, and baked at 240° C. for 60 seconds and further at 400° C. for 120 seconds to thereby form an underlayer film having a film thickness of 80 nm. A resist solution for ArF was coated on the underlayer film, and baked at 130° C. for 60 seconds to thereby form a photoresist layer having a film thickness of 150 nm. Herein, as the resist solution for ArF, one prepared by blending 5 parts by mass of the compound of the following formula (11), 1 part by mass of triphenylsulfonium nonafluoromethanesulfonate, 2 parts by mass of tributylamine, and 92 parts by mass of PGMEA was used.

[Formula 42]

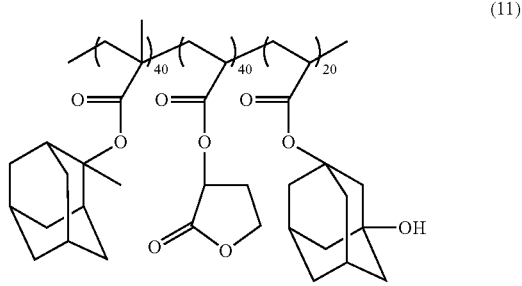

(11)

(in the formula (11), the numerals 40, 40, and 20 indicate the proportions of the respective constituent units, and do not mean a block copolymer.)

Then, the photoresist layer was exposed through a mask by using an electron beam lithography apparatus (ELS-7500, produced by Elionix, Inc., 50 keV), baked at 115° C. for 90 seconds (PEB), and developed with a 2.38% by mass aqueous tetramethylammonium hydroxide (TMAH) solution for 60 seconds, thereby providing a positive-type resist pattern.

Comparative Example 2

Except that no underlayer film was formed, the same manner as in Example 17 was performed to form a photoresist layer on a SiO$_2$ substrate to provide a positive-type resist pattern. The evaluation results are shown in Table 2.

[Evaluation]

The shapes of the resist patterns of 55 nm L/S (1:1) and 80 nm L/S (1:1) provided in each of Examples 17 to 32 and Comparative Example 2 were observed. The results are shown in Table 2.

TABLE 2

| | Material for forming underlayer film | Resolution (nmL/S) | Sensitivity (μC/cm$^2$) | Resist pattern formation after development |
|---|---|---|---|---|
| Example 17 | Material described in Table 1 (Example 1) | 55 | 12 | Good |
| Example 18 | Material described in Table 1 (Example 2) | 55 | 12 | Good |
| Example 19 | Material described in Table 1 (Example 3) | 55 | 12 | Good |
| Example 20 | Material described in Table 1 (Example 4) | 55 | 12 | Good |
| Example 21 | Material described in Table 1 (Example 5) | 55 | 12 | Good |
| Example 22 | Material described in Table 1 (Example 6) | 55 | 12 | Good |
| Example 23 | Material described in Table 1 (Example 7) | 55 | 12 | Good |
| Example 24 | Material described in Table 1 (Example 8) | 55 | 12 | Good |
| Example 25 | Material described in Table 1 (Example 9) | 55 | 12 | Good |
| Example 26 | Material described in Table 1 (Example 10) | 55 | 12 | Good |
| Example 27 | Material described in Table 1 (Example 11) | 55 | 12 | Good |
| Example 28 | Material described in Table 1 (Example 12) | 55 | 12 | Good |
| Example 29 | Material described in Table 1 (Example 13) | 55 | 12 | Good |
| Example 30 | Material described in Table 1 (Example 14) | 55 | 12 | Good |
| Example 31 | Material described in Table 1 (Example 15) | 55 | 12 | Good |
| Example 32 | Material described in Table 1 (Example 16) | 55 | 12 | Good |
| Comparative Example 2 | Not used | 80 | 26 | Not good |

As can be seen from Table 2, it was confirmed that the underlayer films of Examples 17 to 32 were significantly excellent in resolution and sensitivity as compared with Comparative Example 2. In addition, it was confirmed that the shape of the resist pattern after development was also good. Furthermore, it was shown from the difference from the shape of the resist pattern after development that the material for forming an underlayer film for lithography in each of Examples 1 to 16 had good adhesiveness with a resist material.

Examples 33 to 48

The solution of the material for forming an underlayer film for lithography in each of Examples 1 to 16 was coated on a SiO$_2$ substrate having a film thickness of 300 nm, and baked at 240° C. for 60 seconds and further at 400° C. for 120 seconds to thereby form an underlayer film having a film thickness of 80 nm. A silicon-containing intermediate layer material was coated on the underlayer film, and baked at 200° C. for 60 seconds to thereby form an intermediate layer film having a film thickness of 35 nm. Furthermore, the resist solution for ArF used in Example 17 was coated on the intermediate layer film, and baked at 130° C. for 60 seconds to thereby form a photoresist layer having a film thickness of 150 nm. Herein, as the silicon-containing intermediate layer material, a silicon atom-containing polymer described in <Synthesis Example 1> in Japanese Patent Laid-Open No. 2007-226170 was used.

Then, the photoresist layer was exposed through a mask by using an electron beam lithography apparatus (ELS-7500, produced by Elionix, Inc., 50 keV), baked at 115° C. for 90 seconds (PEB), and developed with a 2.38% by mass aqueous tetramethylammonium hydroxide (TMAH) solution for 60 seconds, thereby providing a positive-type resist pattern of 55 nmL/S (1:1).

Thereafter, the silicon-containing intermediate layer film (SOG) was subjected to dry etching processing with the obtained resist pattern as a mask using RIE-10NR manufactured by Samco Inc., and subsequently, dry etching processing of the underlayer film with the obtained silicon-containing intermediate layer film pattern as a mask and dry etching processing of the SiO$_2$ film with the obtained underlayer film pattern as a mask were performed, sequentially.

The respective etching conditions are shown as follows.

Conditions of Resist Pattern Etching on Resist Intermediate Layer Film

Output: 50 W
Pressure: 20 Pa
Time: 1 min
Etching Gas
Ar gas flow rate:CF$_4$ gas flow rate:O$_2$ gas flow rate=50:8:2 (sccm)

Conditions of Resist Intermediate Film Pattern Etching on Resist Underlayer Film
Output: 50 W
Pressure: 20 Pa
Time: 2 min
Etching Gas
Ar gas flow rate:$CF_4$ gas flow rate:$O_2$ gas flow rate=50:5:5 (sccm)
Conditions of Resist Underlayer Film Pattern Etching on $SiO_2$ Film
Output: 50 W
Pressure: 20 Pa
Time: 2 min
Etching Gas
Ar gas flow rate:$C_5F_{12}$ gas flow rate:$C_2F_6$ gas flow rate:$O_2$ gas flow rate=50:4:3:1 (sccm)

[Evaluation]

The cross section of the pattern (the shape of the $SiO_2$ film after etching) of each of Examples 33 to 48 obtained as described above was observed using an electron microscope (S-4800) manufactured by Hitachi Ltd., and it was confirmed that in Examples using the underlayer film of the present invention, the shape of the $SiO_2$ film after etching in multilayer resist processing was rectangular and good with no defects observed.

As described above, the present invention is not limited to the embodiments and Examples, and can be appropriately modified without departing the gist thereof.

It is to be noted that the present application claims the priorities based on Japanese Patent Application (Japanese Patent Application No. 2011-176923) filed to Japan Patent Office on Aug. 12, 2011, Japanese Patent Application (Japanese Patent Application No. 2011-201757) filed to Japan Patent Office on Sep. 15, 2011, and Japanese Patent Application (Japanese Patent Application No. 2011-218440) filed to Japan Patent Office on Sep. 30, 2011, and the contents thereof are herein incorporated as reference.

INDUSTRIAL APPLICABILITY

Since the material for forming an underlayer film for lithography and the underlayer film of the present invention have a relatively high carbon concentration, a relatively low oxygen concentration, a relatively high heat resistance and also a relatively high solvent solubility, and which can be applied to a wet process, they can be widely and effectively utilized in various applications in which these properties are required. Therefore, the present invention can be widely and effectively utilized for, for example, an electric insulating material; a resist resin; a sealing resin for a semiconductor; an adhesive for a printed wiring board; an electric laminated board mounted on electrical equipment, electronic equipment, industrial equipment and the like; a matrix resin for a prepreg mounted on electrical equipment, electronic equipment, industrial equipment and the like; a material for a build-up laminated board; a resin for fiber-reinforced plastics; a sealing resin for a liquid crystal display panel; a paint; various coating agents; an adhesive; a coating agent for a semiconductor; a resist resin for a semiconductor; and a resin for forming an underlayer film, and can be particularly effectively utilized in the field of an underlayer film for lithography and an underlayer film for a multilayer resist.

The invention claimed is:

1. A material for forming an underlayer film for lithography, comprising:
a compound represented by the following general formula (1)

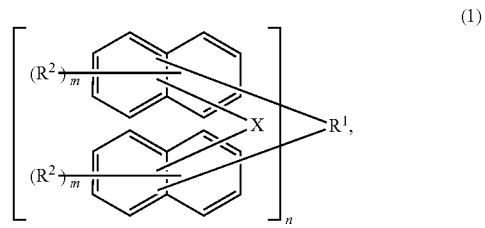

wherein formula (1), each X independently represents an oxygen atom or a sulfur atom, each $R^1$ independently represents a single bond or a 2n-valent hydrocarbon group having 1 to 30 carbon atoms, the hydrocarbon group may have a cyclic hydrocarbon group, a double bond, a hetero atom, or an aromatic group having 6 to 30 carbon atoms, and each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group, each m is independently an integer of 1 to 6, and n is an integer of 1 to 4; and at least one of an acid generating agent and a crosslinking agent.

2. The material for forming an underlayer film for lithography according to claim 1, wherein the compound represented by the general formula (1) is a compound represented by the following general formula (1a

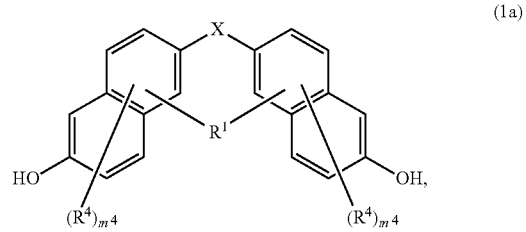

wherein formula (1a), each X independently represents an oxygen atom or a sulfur atom, each $R^1$ independently represents a single bond or a 2n-valent hydrocarbon group having 1 to 30 carbon atoms, the hydrocarbon group may have a cyclic hydrocarbon group, a double bond, a hetero atom, or an aromatic group having 6 to 30 carbon atoms, each $R^4$ independently represents a linear, branched or cyclic alkyl group having 1 to 10 carbon atoms, an aryl group having 6 to 10 carbon atoms, an alkenyl group having 2 to 10 carbon atoms, or a hydroxyl group, and each $m^4$ is independently an integer of 0 to 5.

3. A material for forming an underlayer film for lithography, comprising a resin having a structure represented by the following general formula (2)

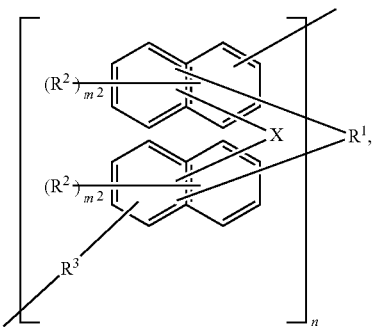

(2)

wherein formula (2), each X independently represents an oxygen atom or a sulfur atom, each $R^1$ independently represents a single bond or a 2n-valent hydrocarbon group having 1 to 30 carbon atoms, the hydrocarbon group may have a cyclic hydrocarbon group, a double bond, a hetero atom, or an aromatic group having 6 to 30 carbon atoms, and each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group, each $R^3$ independently represents a single bond, or a linear or branched alkylene group having 1 to 20 carbon atoms, each $m^2$ is independently an integer of 1 to 5, and n is an integer of 1 to 4.

4. The material for forming an underlayer film for lithography according to claim 1, further comprising an organic solvent.

5. The material for forming an underlayer film for lithography according to claim 1, wherein said material includes an acid generating agent.

6. The material for forming an underlayer film for lithography according to claim 1, wherein said material includes a crosslinking agent.

7. An underlayer film for lithography comprising the material for forming an underlayer film for lithography according to claim 1.

8. A pattern forming method comprising:
   forming an underlayer film on a substrate by applying the material for forming an underlayer film according to claim 1 onto the substrate;
   forming at least one photoresist layer on the underlayer film;
   after forming the at least one photoresist layer, irradiating a region of the photoresist layer with radiation; and
   after irradiating with radiation, developing with an alkali.

9. A pattern forming method comprising:
   forming an underlayer film on a substrate by applying the material for forming an underlayer film according to claim 1 onto the substrate;
   forming an intermediate layer film on the underlayer film by applying a silicon atom-containing resist intermediate layer film material onto the underlayer film;
   forming at least one photoresist layer on the intermediate layer film;
   after forming the at least on photoresist layer, irradiating a required region of the photoresist layer with radiation;
   after irradiating with radiation, developing with an alkali to form a resist pattern; and
   after developing, etching the intermediate layer film while the resist pattern functions as a mask, etching the underlayer film while the obtained intermediate layer film pattern functions as an etching mask and etching the substrate while the obtained underlayer film pattern functions as an etching mask, to form a pattern on the substrate.

* * * * *